United States Patent
Cherry et al.

(10) Patent No.: US 11,587,687 B2
(45) Date of Patent: Feb. 21, 2023

(54) PATIENT COMMUNICATION SYSTEM

(71) Applicant: MOVEMENT FOR LIFE, INC., San Luis Obispo, CA (US)

(72) Inventors: Andrew Cherry, Atascadero, CA (US); James Glinn, Cayucos, CA (US); Kelly Sanders, Atascadero, CA (US)

(73) Assignee: MOVEMENT FOR LIFE, INC., San Luis Obispo, CA (US)

( * ) Notice: Subject to any disclaimer, the term of this patent is extended or adjusted under 35 U.S.C. 154(b) by 126 days.

(21) Appl. No.: 16/909,849

(22) Filed: Jun. 23, 2020

(65) Prior Publication Data
US 2021/0398692 A1 Dec. 23, 2021

(51) Int. Cl.
*G16H 70/20* (2018.01)
*G16H 10/60* (2018.01)
(Continued)

(52) U.S. Cl.
CPC ............ *G16H 70/20* (2018.01); *G16H 10/60* (2018.01); *G16H 50/30* (2018.01); *G16H 80/00* (2018.01)

(58) Field of Classification Search
CPC ........ G16H 70/20; G16H 50/30; G16H 80/00; G16H 10/60
(Continued)

(56) References Cited

U.S. PATENT DOCUMENTS

2004/0078236 A1* 4/2004 Stoodley ............... G16H 70/20
705/2
2005/0027567 A1 2/2005 Taha
(Continued)

FOREIGN PATENT DOCUMENTS

WO WO-2017147652 A1 * 9/2017 ............... A61B 5/01

OTHER PUBLICATIONS

Feldman, Keith Joseph; Beyond Modeling: The Emergent Role of Informatics in Advancing Healthcare Knowledge; University of Notre Dame. ProQuest Dissertations Publishing, 2018. 13836446. (Year: 2018).*

(Continued)

*Primary Examiner* — Hiep V Nguyen
(74) *Attorney, Agent, or Firm* — Fitch, Even, Tabin & Flannery LLP

(57) ABSTRACT

The techniques described herein may provide for an evidence-based, clinical practice guideline-driven, patient communication system. A user (e.g., a patient, a client, etc.) may interact with, or use, a patient communication system for improved healthcare according to one or more aspects. The patient communication system may credibly categorize user inputs into injury patterns (e.g., correlated to healthcare industry established clinical practice guidelines). For instance, an evidence-based, clinical practice guideline-driven, patient communication system may utilize a library of extensive and credible healthcare information (e.g., reviewed by a credible body established by the healthcare industry). Such information may include physical therapy videos, recovery strategies, workplace group or client-group healthcare information, etc. The patient communication system may generate (e.g., based on user input and decision-making trees) patient diagnosis, injury recovery plans, wellness plans, healthcare information reports (e.g., for healthcare clinicians, insurance companies, employers, etc.), and preventative healthcare plans, among other examples.

16 Claims, 10 Drawing Sheets

(51) Int. Cl.
  *G16H 50/30* (2018.01)
  *G16H 80/00* (2018.01)
(58) Field of Classification Search
  USPC .............................................................. 705/3
  See application file for complete search history.

(56) References Cited

U.S. PATENT DOCUMENTS

| | | | |
|---|---|---|---|
| 2010/0056875 A1 | 3/2010 | Schoenberg | |
| 2010/0241464 A1 | 9/2010 | Amigo | |
| 2010/0330537 A1* | 12/2010 | Gibbs | G06Q 10/06 705/2 |
| 2014/0006045 A1* | 1/2014 | Wund, II | G16H 15/00 705/2 |
| 2015/0302766 A1 | 10/2015 | Oberlander | |

OTHER PUBLICATIONS

PCT; International Search Report and Written Opinion of the International Searching Authority dated Jun. 2, 2021.
"Adhesive Capsulitis: Clinical Practice Guidelines"; Journal of Orthopaedic & Sports Physical Therapy; May 2013; vol. 43, No. 5; p. A26; Downloaded from www.jospt.org on Apr. 19, 2018.
"Ankle Ligament Sprain: Clinical Practice Guidelines"; Journal of Orthopaedic & Sports Physical Therapy; Sep. 2013; vol. 43, No. 9; pp. A29-A30; Downloaded from www.jospt.org on Apr. 19, 2018.
"Exercise-Based Knee and Anterior Cruciate Ligament Injury Prevention: Clinical Practice Guidelines"; Journal of Orthopaedic & Sports Physical Therapy; Sep. 2018; vol. 48, No. 9; p. A2; Downloaded from www.jospt.org on Sep. 4, 2018.
"Heel Pain—Plantar Fasciitis: Clinical Practice Guidelines Revision 2014"; Journal of Orthopaedic & Sports Physical Therapy; Nov. 2014; vol. 4, No. 11; pp. A2-A3; Downloaded from www.jospt.org on Apr. 19, 2018.
"Hip Pain, Mobility Deficits, Osteoarthritis: Clincal Practice Guidelines Revision 2017"; Journal of Orthopaedic & Sports Physical Therapy; Jun. 2017; vol. 47, No. 6; pp. A2-A3; Downloaded from www.jospt.org on Jun. 12, 2017.
Knee Ligament Sprain: Clinical Practice Guidelines Revision 2017; Journal of Orthopaedic & Sports Physical Therapy; Nov. 2017; vol. 47, No. 11; pp. A2-A3; Downloaded from www.jospt.org on Apr. 19, 2018.
"Knee Pain and Mobility Impairments: Clinical Practice Guidelines Revision 2018"; Journal of Orthopaedic & Sports Physical Therapy; Feb. 2018; vol. 48, No. 2; p. A2; Downloaded from www.jospt.org on Apr. 19, 2018.
"Low Back Pain: Clincial Practice Guidelines"; Journal of Orthopaedic & Sports Physical Therapy; Apr. 2012; vol. 42, No. 4; A44-A46; Downloaded from www.jospt.org on Apr. 19, 2018.
"Midportion Achilles Tendinopathy: Clinical Practice Guidelines Revision 2018"; Journal of Orthopaedic & Sports Physical Therapy; May 2018; vol. 48, No. 5; p. A2; Downloaded from www.jospt.org on Jun. 12, 2018.
"Neck Pain: Clinical Practice Guidelines Revision 2017"; Journal of Orthopaedic & Sports Physical Therapy; Jul. 2017; vol. 47, No. 7; p. A2-A3; Downloaded from www.jospt.org on Apr. 19, 2018.
"Nonarthritic Hip Joint Pain: Clinical Practice Guidelines"; Journal of Orthopaedic & Sports Physical Therapy; Jun. 2014; vol. 44, No. 6; p. A25; Downloaded from www.jospt.org on Apr. 19, 2018.
Erickson, et al.; "Hand Pain and Sensory Deficits: Carpal Tunnel Syndrome"; Journal of Orthopaedic & Sports Physical Therapy; May 2019; vol. 49, No. 5; 3 pages Downloaded from www.jospt.org on May 15, 2019.
Hinge Health; "The World's First Digital Clinic for Back and Joint Pain"; Jun. 4, 2020; downloaded from https://hingehealth.com/ on Oct. 20, 2020; 7 pages.
Kaplan et al; "Summary and Status of Action Statements for the 2018 Congenital Muscular Torticollis Clinical Practice Guideline"; Pediatric Physical Therapy; Academy of Pediatric Physical Therapy of the American Physical Therapy Association; 2018; pp. 246-248.
Physera; "A better way to treat & prevent pain"; Jun. 17, 2020; downloaded from https://physera.com/ on Oct. 20, 2020; 6 pages.
Physio U; "Top-Rated Rehab Guide for Student & Professional"; Jul. 11, 2017; downloaded from https://www.physiou.health on Oct. 20, 2020; 7 pages.
Physiotools; "Physiotools Exercise Software-Key Features"; Mar. 30, 1997; downloaded from https://www.physiotools.com/physiotools-exercise-software-key-features# on Dec. 18, 2020; 4 pages.
Phzio; "Phzio—Virtual Care"; May 26, 2020; downloaded from https://phzio.com on Oct. 20, 2020; 8 pages.
RecoveryOne; "Digital Musculoskeletal Platform"; Apr. 30, 2020; downloaded from https://recoveryone.com on Oct. 20, 2020; 6 pages.
Rehab Therx; Mar. 29, 2020; downloaded from https://www.rehabtherx.com on Dec. 18, 202; 3 pages.
Willy, et al.. "Patellofemoral Pain"; Journal of Orthopaedic & Sports Physical Therapy; Sep. 2019; vol. 49, No. 9; 5 pages; Downloaded from www.jospt.org on Sep. 9, 2019.

\* cited by examiner

Identify My Injury

Answer some questions and receive a personalized series of evidence-based and physical therapists curated exercises designed to empower you to gently alleviate the pain for 23 of the most commonly reported ailments. If you do not fit into an injury pattern, you can access self-help with our Generalized Plans, find a physical therapy clinic near you, or have a visit with a live provider online.

Select one body part where you are having problems:

305

Front          Back

Recovery Strategies

Shoulder Instability Recovery Plan
17.01 Back and Ribs Self-Mobilization: Chair stretch (Shoulder Movement Coordination Impairments) Pattern©

⊡ Beginner
⊡ Average
⊡ Advanced

Shoulder Instability Recovery Plan
17.01 Back and Ribs Self-Mobilization: Chair stretch (Shoulder Movement Coordination Impairments) Pattern

Key Points of Exercise:
- Sit with back resting against a firm, strong chair
- Place hands behind your head, and perform a chin tuck
- Bend backward
- The goal is to feel a stretch in your upper back

Reps:
- 6 Repetitions

Equipment:
- Chair with firm back rest

ⓘ Learn More    ♡ Add to Favorites

Up Next    Difficulty 17.01 Back and Ribs Self-Mobilization: Chair stretch    ⊡

09.01 Shoulder Internal Rotation Stretch:Sleeper Position    ⊡

11.01 Scapular Upward Rotation: Lower Trapezius - standing wall lifts    ⊡

13.03 Scapular Stabilization: Serratus Anterior - quadruped arm lifts    ⊡

15.01 Shoulder External Rotation: Infraspinatus sidelying    ⊡

16.02 Shoulder Internal Rotation: Subscapularies - arm at side    ⊡

Shoulder Instability Recovery Plan

From the information you provided, it sounds like you have a stiff, and maybe painful neck. Having a stiff neck can be bothersome and can limit your daily life. The condition can result from "sleeping wrong," from turning your head too quickly or awkwardly, or from the normal healing processes following an injury, such as a fall or a collision. Individuals often have pain primarily on one side of their neck and have a difficult time turning their head fully in one or more directions.

The joints and muscles in your neck work together to allow you to move freely. When a problem occurs in the joints in your upper back and neck, the muscles near the affected joints tend to tighten up to prevent you from moving your neck and further injuring yourself. This is helpful to promote healing for a couple of days; but afterward, those same muscles need to be trained to return to their normal ways of moving-without abnormal restrictions and pain. In the medical world, this stiffness betw een one vertebrae, or segment, of the spine and the adjacent segment is given the term "segmental mobility deficit."

What to do...
A great way to "deal with a stiff neck is to exercise, especially the stretching exercises that we provide for you. We suggest that you start with the Segmental SNAG that you perform sitting and the Diagonal and Side Neck Stretches that you perform while lying down - the Beginning Level exercises. With the Diagonal and Side Neck Stretches, a feeling of stretching or pulling while performing the exercises is fine, but you should not have intense pain during the stretching. Nor should you feel ach y or stiff 20 minutes after you have finished your exercise routine. As shown in the videos, hold the stretches for about 30 seconds. After you feel comfortable with performing the stretching exercises while lying down, progress to performing the neck stretches in the sitting position - the Progressing Level exercises.

FIG. 4

Patient Name: Andrew Cherry
Patient Date of Birth: 11/08/1974
Zip Code:
Registration Date: 04/01/2020
Gender: NotSpecified
Group Name: Express (pay online) Plan 2
Most Recent Recovery Plan Strategy Provider Assigned: Neck Stiffness Recovery Plan (04/08/2020)
Most Recent Recovery Plan Strategy Self-Assigned: Neck Stiffness Recovery Plan (04/08/2020)

| Pre-teleconference Question | Identify Your Injury | Create Exercise Playlist | Provider Notes |

Show 50 entries                                    Search:

| Body Region ⇵ | Question | ⇵ User Answer | ⇵ Date |
|---|---|---|---|
| Shoulder | Is the discomfort in your shoulder constantly present, or does that discomfort come and go? | Come & Go | 04/14/20 08:37:00 |
| Shoulder | Does moving your shoulder or changing the position of your shoulder affect your symptoms? | Yes | 04/14/20 08:37:00 |
| Shoulder | Does your shoulder joint feel unstable or have you ever dislocated your shoulder? | Yes | 04/14/20 08:37:00 |
| Shoulder | Is the discomfort in your shoulder constantly present, or does that discomfort come and go? | Come & Go | 04/08/20 15:44:00 |
| Shoulder | Does moving your shoulder or changing the position of your shoulder affect your symptoms? | Yes | 04/08/20 15:44:00 |
| Shoulder | Does your shoulder joint feel unstable or have you ever dislocated your shoulder? | Yes | 04/08/20 15:44:00 |
| Shoulder | Is the discomfort in your shoulder constantly present, or does that discomfort come and go? | Come & Go | 04/01/20 12:01:00 |
| Shoulder | Does moving your shoulder or changing the position of your shoulder affect your symptoms? | Yes | 04/01/20 12:01:00 |
| Shoulder | Does your shoulder joint feel unstable or have you ever dislocated your shoulder? | Yes | 04/01/20 12:01:00 |

Showing 1 to 9 of 9 entries                               First Previous [1] Next Last

PATIENT COMMUNICATION SYSTEM

BACKGROUND OF THE INVENTION

1. Field of the Invention

The present invention relates generally to patient communication, and more specifically to an evidence-based, clinical practice guideline-driven, patient communication system.

2. Discussion of the Related Art

Various systems and processes are known in the art for patient communication systems.

Conventional patient analysis and patient healthcare has been limited by several factors such as healthcare cost, consultant availability (e.g., time resources of clinicians who are trained in healthcare assessment and treatment), etc. Recent adoption of electronic health records has driven a significant increase in the amount of available digital healthcare data. Such healthcare data may be leveraged to explore new avenues in advancing healthcare, create new efficiencies in healthcare, improve patient care, etc.

SUMMARY

A system for an evidence-based, clinical practice guideline-driven, patient communication is described. Embodiments of the system may include a patient information collection system including: an input device; a first output device; a first code segment, wherein the first code segment is coupled to the input device to receive input from a patient via the input device, and wherein the first code segment is coupled to the first output device, wherein the first code segment comprises a sequence of instructions, and wherein the sequence of instructions comprises: a first instruction to prompt the patient to input a first input using the first output device; a second instruction to prompt the patient to input a second input using the first output device; a third instruction to prompt the patient to input a third input using the first output device, a database coupled to the patient information collection system, wherein the first code segment associates the first input, the second input, and the third input with a unique identifier for uniquely identifying the patient, and stores the first input, the second input, and the third input with the unique identifier into the database, a patient clinical injury recovery plan generator coupled to the database, wherein the patient clinical injury recovery plan generator comprises: a second code segment, wherein the second code segment reads the unique identifier, the first input, the second input, and the third input from the database, and searches to match the first input, the second input, and the third input to a patient clinical injury recovery plan; and a second output device, wherein the second output device is configured to output the patient clinical injury recovery plan, and a population targeting system coupled to the database, wherein the population targeting system comprises: a third code segment, wherein the third code segment reads the unique identifier, the first input, the second input, and the third input from the database, reads other data from the database, and aggregates the first input, the second input, and the third input with the other data to identify targeted prevention strategies for groups of patients in a particular work role having risks of developing musculoskeletal overuse conditions or injuries.

A system for an evidence-based, clinical practice guideline-driven, patient communication system is described. Embodiments of the system may include a patient information collection system including: an input device; a first output device; a first code segment, wherein the first code segment is coupled to the input device to receive input from a patient via the input device, and wherein the first code segment is coupled to the first output device, wherein the first code segment comprises a sequence of instructions, and wherein the sequence of instructions comprises: a first instruction to prompt the patient to input a first input using the first output device; a second instruction to prompt the patient to input a second input using the first output device; a third instruction to prompt the patient to input a third input using the first output device, a database coupled to the patient information collection system, wherein the first code segment associates the first input, the second input, and the third input with a unique identifier for uniquely identifying the patient, and stores the first input, the second input, and the third input with the unique identifier into the database, a patient clinical injury recovery plan generator coupled to the database, wherein the patient clinical injury recovery plan generator comprises a second code segment, wherein the second code segment reads the unique identifier, the first input, the second input, and the third input from the database, and searches to match the first input, the second input, and the third input to a patient clinical injury recovery plan; and a second output device, wherein the second output device is configured to output the patient clinical injury recovery plan, a risk classifier system coupled to the database, wherein the risk classifier system comprises: a third code segment, wherein the third code segment reads the unique identifier, the first input, the second input, and the third input from the database, and identifies patients at risk of progressing to disabling, chronic or costly conditions and identifies care pathways appropriate to mitigating the progressing to disabling, chronic or costly conditions, and a clinician reporting system, wherein the clinician reporting system comprises: a fourth code segment, wherein the fourth code segment reads the unique identifier, the first input, the second input, and the third input from the database, and generates a clinician report; and a third output device, wherein the third output device is configured to output the clinician report.

A system for an evidence-based, clinical practice guideline-driven, patient communication is described. Embodiments of the system may include a patient information collection system including: an input device; a first output device; a first code segment, wherein the first code segment is coupled to the input device to receive input from a patient via the input device, and wherein the first code segment is coupled to the first output device, wherein the first code segment comprises a sequence of instructions, and wherein the sequence of instructions comprises: a first instruction to prompt the patient to input a first input using the first output device; a second instruction to prompt the patient to input a second input using the first output device; a third instruction to prompt the patient to input a third input using the first output device, a database coupled to the patient information collection system, wherein the first code segment associates the first input, the second input, and the third input with a unique identifier for uniquely identifying the patient, and stores the first input, the second input, and the third input with the unique identifier into the database, a patient clinical injury recovery plan generator coupled to the database, wherein the patient clinical injury recovery plan generator comprises: a second code segment, wherein the second code segment reads the unique identifier, the first input, the second input, and the third input from the database, and searches to match the first input, the second input, and the third input to a patient clinical injury recovery plan; and a second output device, wherein the second output device is configured to output the patient clinical injury recovery plan, a population targeting system coupled to the database, wherein the population targeting system comprises a third code segment, wherein the third code segment reads the unique identifier, and the first input, the second input and the third input from the database, reads other data from the database, and aggregates the first input, the second input, and the third input with the other data to identify targeted prevention strategies for groups of patients in a particular work role having risks of developing musculoskeletal overuse conditions or injuries, and a risk classifier system coupled to the database, wherein the risk classifier system comprises: a fourth code segment, wherein the fourth code segment reads the unique identifier, the first input, the second input, and the third input from the database, and identifies patients at risk of progressing to disabling, chronic or costly conditions and identifies care pathways appropriate to mitigating the progressing to disabling, chronic or costly conditions.

A method, apparatus, and non-transitory computer readable medium for evidence-based, clinical practice guideline-driven, patient communication is described. Embodiments of the method, apparatus, and non-transitory computer readable medium may receive input from a patient via an input device comprising: prompting the patient to input a first input using a first output device; prompting the patient to input a second input using the first output device; prompting the patient to input a third input using the first output device, associate the first input, the second input, and the third input with a unique identifier for uniquely identifying the patient, store the first input, the second input, and the third input with the unique identifier into a database, read the unique identifier, the first input, the second input, and the third input from the database, search to match the first input, the second input, and the third input to a patient clinical injury recovery plan, output the patient clinical injury recovery plan, and aggregate the first input, the second input, and the third input with other data to identify targeted prevention strategies for groups of patients in a particular work role having risks of developing musculoskeletal overuse conditions or injuries.

A method, apparatus, and non-transitory computer readable medium for evidence-based, clinical practice guideline-driven, patient communication is described. Embodiments of the method, apparatus, and non-transitory computer readable medium may receive input from a patient via an input device comprising: prompting the patient to input a first input using a first output device; prompting the patient to input a second input using the first output device; prompting the patient to input a third input using the first output device, associate the first input, the second input, and the third input with a unique identifier for uniquely identifying the patient, store the first input, the second input, and the third input with the unique identifier into a database, search to match the first input, the second input, and the third input to a patient clinical injury recovery plan, output the patient clinical injury recovery plan, identify patients at risk of progressing to disabling, chronic or costly conditions as a function of the first input, the second input, and the third input from the database, identify care pathways for the patients at risk appropriate to mitigating the progressing to disabling, chronic or costly conditions, generate a clinician report as a function of the first input, the second input, and the third input from the database, and output the clinician report.

A method, apparatus, and non-transitory computer readable medium for evidence-based, clinical practice guideline-driven, patient communication is described. Embodiments of the method, apparatus, and non-transitory computer readable medium may receive input from a patient via an input device comprising: prompting the patient to input a first input using a first output device; prompting the patient to input a second input using the first output device; prompting the patient to input a third input using the first output device, associate the first input, the second input, and the third input with a unique identifier for uniquely identifying the patient, store the first input, the second input, and the third input with the unique identifier into a database, search to match the first input, the second input, and the third input to a patient clinical injury recovery plan, output the patient clinical injury recovery plan, identify patients at risk of progressing to disabling, chronic or costly conditions as a function of the first input, the second input, and the third input from the database, and identify care pathways for the patients at risk appropriate to mitigating the progressing to disabling, chronic or costly conditions.

BRIEF DESCRIPTION OF THE DRAWINGS

FIG. 3 shows an example of a screen display according to aspects of the present disclosure.

FIG. 4 shows an example of a patient clinical injury recovery plan according to aspects of the present disclosure.

FIG. 5 shows an example of a clinician report according to aspects of the present disclosure.

DETAILED DESCRIPTION

Figure 1:
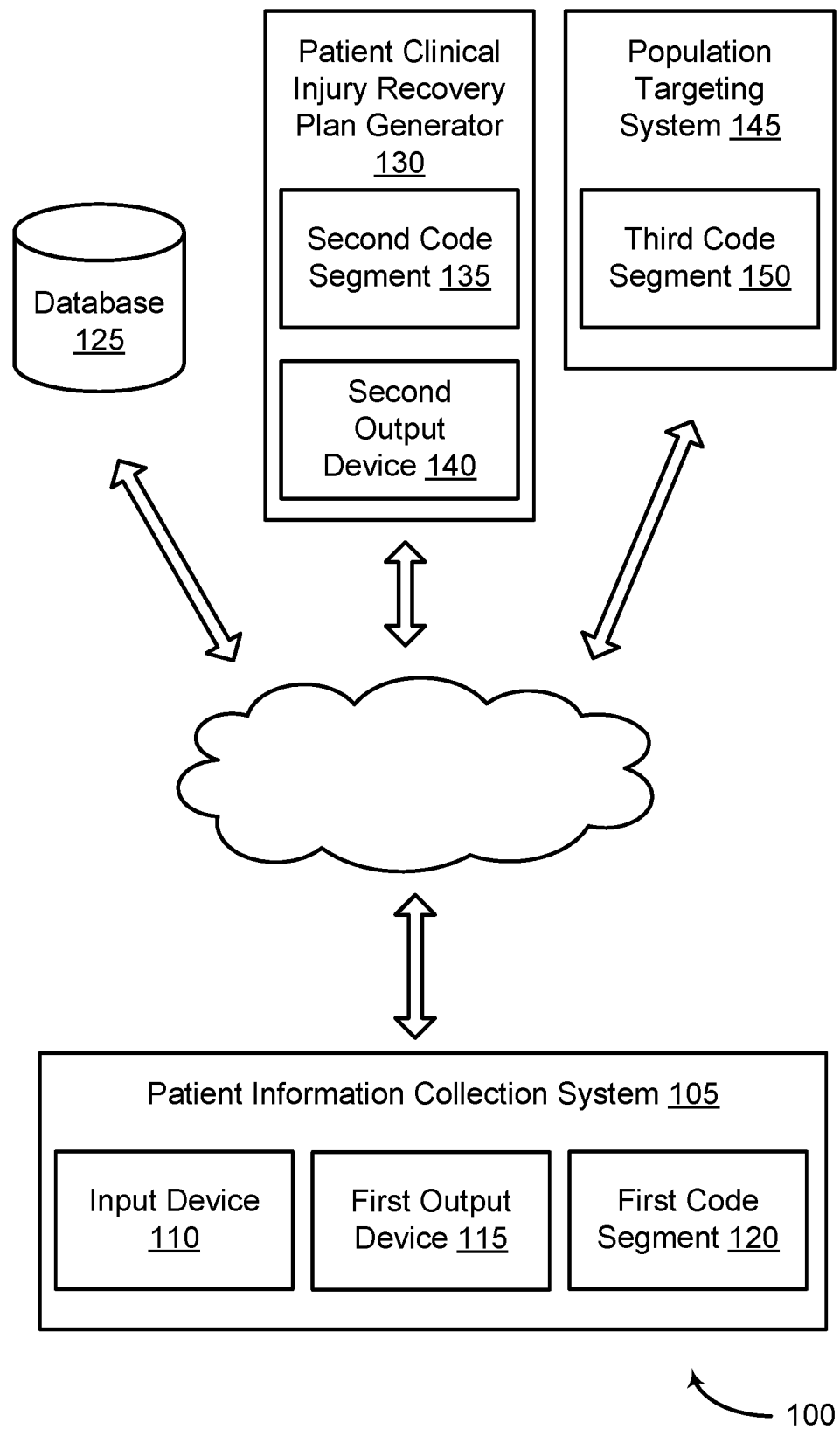
FIG. 1 shows an example of a patient communication system according to aspects of the present disclosure.

The following description is not to be taken in a limiting sense, but is made merely for the purpose of describing the general principles of exemplary embodiments. The scope of the invention should be determined with reference to the claims.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Conventional patient analysis and patient healthcare have been limited by several factors such as healthcare cost, consultant availability (e.g., time resources of clinicians who are trained in healthcare assessment and treatment), severity of symptoms or identification of symptoms, among other examples. For instance, healthcare costs may be inflated (e.g., or relatively higher) when a patient is analyzed and diagnosed by a consultant compared to costs associated with other means of healthcare (e.g., such as self-help healthcare, automated analysis and diagnosis, etc.). In some cases, healthcare consultants (e.g., such as doctors, clinicians, therapists, etc.) may be limited in availability, may have limitations in a number of approved patients, may have limitations in medical equipment or office space, etc. Further, conventional healthcare techniques may be deficient in terms of preemptive healthcare, as patients may not seek healthcare attention until symptoms become severe or uncomfortable.

Recent adoption of electronic health records has driven a significant increase in the amount of available digital healthcare data. Such healthcare data may be leveraged to explore new avenues in advancing healthcare, create new efficiencies in healthcare, improve patient care, etc. However, providing healthcare may be associated with important ethical and credibility considerations. For instance, self-help healthcare or automated healthcare, which may not necessarily be personally supervised by a qualified healthcare consultant, may be associated with credibility considerations such as, for example, the accuracy of diagnosis and the accuracy of provided therapy or medical advice.

The techniques described herein may provide for an evidence-based, clinical practice guideline-driven, patient communication system. A user (e.g., a patient, a client, etc.) may interact with, or use, a patient communication system for improved healthcare according to one or more aspects. For instance, the techniques described herein may provide for reduced healthcare costs, expedited diagnosis and healthcare planning, efficient triage of patients or patient-groups, and improved preventative healthcare techniques, among various other efficiencies in providing patient healthcare.

As discussed in more detail below, the described evidence-based, clinical practice guideline-driven, patient communication system may credibly categorize user inputs into injury patterns (e.g., correlated to healthcare industry established clinical practice guidelines). For instance, an evidence-based, clinical practice guideline-driven, patient communication system may utilize a library of extensive and credible healthcare information (e.g., reviewed by a credible body established by the healthcare industry). Such information may include physical therapy videos, recovery strategies, workplace group or client-group healthcare information, etc. The patient communication system may generate (e.g., based on user input and decision-making trees) patient diagnosis, injury recovery plans, wellness plans, healthcare information reports (e.g., for healthcare clinicians, insurance companies, employers, etc.), and preventative healthcare plans, among other examples.

FIG. 1 shows an example of a system for patient communication according to aspects of the present disclosure. Patient communication system 100 may include patient information collection system 105, database 125, patient clinical injury recovery plan generator 130, and population targeting system 145.

A user may interact with patient communication system 100 to develop a patient recovery plan. For instance, a user may refer to a patient, a client, a beneficiary, a consultant, a clinician, an insurance company or insurance agent, or any user of the patient communication system 100. The user may communicate or interface with the patient communication system 100, and the patient communication system 100 may process the user (e.g., inputs from the user via input device 110) for various healthcare applications as described herein. For instance, the user may interface with the patient communication system 100 to receive healthcare plans, injury recovery plans, injury prevention plans, etc. In some cases, the patient communication system 100 may obtain healthcare data from the user for pattern recognition, identification of at-risk groups, identification of work-specific health-literate education, etc., as described in more detail herein. Generally, user interfacing with the patient communication system 100 may include user input of information to the patient communication system 100 (e.g., and in some cases may also include patient communication system 100 output of healthcare information to the user via first output device 115, second output device 140, or both).

In some examples, a user may be run through (e.g., processed by) a self-help procedure (e.g., a self-help algorithm) of injury identification questions based on user input (e.g., based on a user's inputted answers to various questions). In some examples, the patient communication system 100 may categorize the one or more inputs as corresponding to an injury pattern (e.g., to one of 23 injury patterns), where injury patterns may be correlated to the Academy of Orthopedic Physical Therapy (AOPT) guidelines, the Journal of Orthopedic and Sports Physical Therapy (JOSPT) guidelines, etc. In some examples, the patient communication system 100 may determine that the one or more inputs do not correlate to an identifiable injury pattern, and the patient communication system 100 may determine that the one or more inputs (e.g., the patient's presentation) may not be supported in a self-help manner. In some cases, where no injury pattern correlation is determined, the patient communication system 100 may indicate the user should see a consultant or health care professional (e.g., and in some embodiments the patient communication system 100 may generate a clinical referral, which may or may not be based on the one or more user inputs).

Patient communications system 100 may include or employ (e.g., via database 125) a library or database of exercise recovery information. For instance, patient communications system 100 may manage, via database 125, a library of physical therapy videos (e.g., including full length videos, videos narrated by a credible clinician such as a physical therapist, etc.). Patient communications system 100 may generate or put together strategies such as recovery strategies, injury recovery plans, wellness plans, preventative healthcare plans, etc., using the library (e.g., based on user input). In some examples, such strategies may be unique for each injury (e.g., for each combination of one or more inputs from a user) and patient communications system 100 may put together various healthcare information based on determined strategies. For instance, patient communication system 100 may determine or generate, based on one or more inputs from a user, a string of exercises, educational information, or other healthcare information, from beginning to advanced, that promote recovery from a particular type of injury.

In some cases, the prescriptive structure may be evidence-based and may allow a user to self-adjust the difficulty level at the end of each exercise (e.g., where user input, such as a user's difficulty adjustment input, may be used by the patient communications system 100 to adjust the string of exercises, the combination of exercises, the intricacy of presented educational information, etc.). Such may enable users to progress toward recovery at their own pace without having to go to a clinician every time for adjustments in exercise, for clarification of diagnosis or other educational information, etc. (e.g., which may significantly reduce costs associated with follow-up consultations).

For instance, a particular user input (e.g., or a particular combination of user input) may be associated with several exercises with varying level of difficulty. In such cases, the patient information system 100 may prompt difficulty or advancement questions such that user input response to such questions may progress the user to more advanced exercises, maintain previously output exercises, or output less advanced exercises (e.g., less physically intensive exercises or exercises projected by the patient communication system 100 to be less painful). By analogy, varying levels or varying intricacy of healthcare educational information may be provided or included in an injury recovery plan based on user indication of understanding or interest.

As described herein, the output of patient communication system 100 (e.g., strategies) may include various healthcare information such as healthcare exercises, healthcare education, clinical referrals, etc. Further, the library (e.g., or database 125) may include the healthcare information from which the strategies are determined, assembled, etc. The library may be a database of credible peer reviewed information. For example, the library may include diagnosis information, exercise information, educational information, and other healthcare information. The library may be correlated to the AOPT guidelines, JOSPT guidelines, other credible healthcare industry guidelines, or some combination thereof. As such, patient communication system 100 may provide for a credible self-care system for efficiently providing healthcare to users.

The techniques described herein may reduce healthcare costs (e.g., for patients, payers, etc.) via implementation in a self-utilization tool that may direct a user to a less expensive form of recovery (e.g., compared to more traditional clinician visits, compared to less efficient preventative healthcare techniques, etc.). Generally, patient communications system 100 may be implemented in any of a variety of ways. In some cases, patient communications system may be implemented as a standalone solution that may be accessed through an application programming interface (API) by health and wellness platforms.

Generally, the techniques described herein may be implemented to categorize patients using decision trees (e.g., which may be implemented via first code segment 120, second code segment 135, third code segment 150, additional or alternative code segments, or any combination thereof). Based on results, the described techniques may be used to assign professionally curated recovery plans. Additionally or alternatively, one or more aspects of the described techniques may be implemented in clinical offices or establishments (e.g., brick and mortar clinics). For instance, patient communication system 100 may expedite intake and initial evaluations by letting a clinician or clinician office know the likely injury before starting a patient consultation.

In some cases, the described techniques may be used as a utilization tool for insurance groups to help determine and define pre-approved visit numbers (e.g., which may be increased due to efficiencies introduced by these techniques). Patient communication system 100 may offer a significantly cheaper option for recovery and may offer insurance groups access to workplace groups or client-groups that may benefit from preventative healthcare measures, among other examples. In some examples, the patient communications system 100 and the described techniques may provide means for practices (e.g., clinical practices) to take and manage contracts with strict visit limits, bundled payment limits, and capitations. Moreover, in some examples these techniques may allow clinicians (e.g., physical therapy offices) to triage patients based on patient need, severity of patient diagnosis, severity of patient symptoms, etc. Further, in some examples, the described techniques may allow clinicians the ability to get patients (e.g., users of patient communication system 100) started early and quickly on healthcare (e.g., recovery) when the patients may have issues or delays in accessing clinicians.

For instance, in example patient communication system 100, a patient (e.g., a user) may be prompted by a first output device 115 (e.g., which may include a display), to input information (e.g., answer one or more questions) via input device 110. The patient communication system 100 may include first code segment 120 that may be coupled to the input device 110 to receive input from a patient via the input device 110. The first code segment 120 may be coupled to the input device 110 to receive input from a patient via the input device 110. The first code segment 120 may include a sequence of instructions.

The sequence of instructions may include a first instruction to prompt the patient to input a first input, using the first output device 115 (e.g., a question or instruction may be prompted to the patient using the first output device 115, and the first output device 115 may thus prompt the patient to input a first input via input device 110). The sequence of instructions may include a second instruction to prompt the patient to input a second input, using the first output device 115 (e.g., a second question or instruction may be prompted to the patient using the first output device 115, and the first output device 115 may thus prompt the patient to input a second input via input device 110). The sequence of instructions may include a third instruction to prompt the patient to input a third input, using the first output device 115 (e.g., a third question or instruction may be prompted to the patient using the first output device 115, and the first output device 115 may thus prompt the patient to input a third input via input device 110).

Patient information collection system 105 may include input device 110, first output device 115, and first code segment 120. Patient information collection system 105 may receive input from a patient via an input device 110. For instance, patient information collection system 105 may, using the first output device 115 to communicate to the patient, prompt the patient to input a first input, prompt the patient to input a second input, and prompt the patient to input a third input. The first input, second input, and third input may be input by the patient via input device 110 (e.g., based on the prompting, which may be displayed via first output device 115). Patient information collection system 105 may also associate the first input, the second input, and the third input with a unique identifier for uniquely identifying the patient. In some examples, the one or more inputs (e.g., first input, second input, third input, or some combination thereof) may include healthcare information, patient or user information, answers to healthcare questions, injury related information, questionnaire responses, etc.

Database 125 may be coupled to the patient information collection system 105. The first code segment 120 may associate the first input, the second input, and the third input with a unique identifier for uniquely identifying the patient. The first code segment 120 may store the first input, the second input, and the third input with the unique identifier into the database 125.

Database 125 may store the first input, the second input, and the third input with the unique identifier into a database 125. Database 125 may also read the unique identifier, the first input, the second input, and the third input from the database 125. Database 125 may also search (e.g., patient communication system 100 may search database 125) to match the first input, the second input, and the third input to a patient clinical injury recovery plan. In general, patient communication system 100 may search database 125 and generate healthcare information based on processing and matching the first input, the second input, and the third input (e.g., with various healthcare information of database 125). In some examples, database 125 may also generate a clinician referral when the searching (e.g., the searching to match the first input, the second input, and the third input to a patient clinical injury recovery plan) results in no match to a patient clinical injury recovery plan.

Patient clinical injury recovery plan generator 130 may be coupled to the database 125. The patient clinical injury recovery plan generator 130 may include a second code segment 135 and a second output device 140. The second code segment 135 may read the unique identifier, the first input, the second input, and the third input from the database 125, and search to match the first input, the second input, and the third input to a patient clinical injury recovery plan. The second output device 140 may be configured to output the patient clinical injury recovery plan. In some cases, the second output device 140 may include the first output device 115.

In some examples, the patient clinical injury recovery plan generator 130 includes the second code segment 135. The second code segment 135 may read the unique identifier, the first input, the second input, and the third input from the database 125. The second code segment 135 may search to match the first input, the second input, and the third input to a patient clinical injury recovery plan. In some cases, when the second code segment 135 searches to match the first input, the second input, and the third input to a patient clinical injury recovery plan, no match to a patient clinical injury recovery plan is made and, in response to the no match to a clinical guidelines-based recovery plan being made, a clinician referral may be generated.

In some examples, the patient clinical injury recovery plan generator 130 includes the second output device 140. The second output device 140 may be configured to output the patient clinical injury recovery plan, where the patient clinical injury recovery plan includes at least one instructional video selected as a function of the first input, the second input, and the third input.

Patient clinical injury recovery plan generator 130 may output the patient clinical injury recovery plan. In some examples, the patient clinical injury recovery plan includes at least one instructional video, illustration, audio file, written instruction, etc. (e.g., various healthcare information may be selected and generated as a function of the first input, the second input, and the third input).

Patient clinical injury recovery plan generator 130 may include second code segment 135 and second output device 140. Patient clinical injury recovery plan generator 130 may reference database 125 to determine healthcare information based on the one or more user inputs (e.g., based on the first, second, and third inputs from a patient).

Population targeting system 145 may be coupled to the database 125. The population targeting system 145 may include a third code segment 150. The third code segment 150 may read the unique identifier, the first input, the second input, and the third input from the database 125. The third code segment 150 may read other data from the database 125 (e.g., such as stored credible healthcare information, which may include AOPT/JOSPT healthcare information such as videos, exercises, educational information, healthcare plants, etc.). In some examples, the third code segment 150 may aggregate the first input, the second input, and the third input with the other data to identify targeted prevention strategies for groups of patients in a particular work role (e.g., workplace groups) having risks of developing musculoskeletal overuse conditions or injuries.

Population targeting system 145 may be coupled to the database 125, wherein the population targeting system 145 comprises: a sixth code segment, wherein the sixth code segment reads the unique identifier, the first input, the second input, and the third input from the database 125, reads other data from the database 125, and aggregates the first input, the second input, and the third input with the other data to identify targeted prevention strategies for groups of patients in a particular work role having risks of developing musculoskeletal overuse conditions or injuries.

In order to identify targeted prevention strategies, assessment and registration data is collected, and the data is combined to identify domains in which the patient may be at risk. The data is collected through the Patient Information Collection System 105 or other relevant biometric data collection means, e.g., a blood pressure monitor, thermometer, scale, heart rate monitor, electrocardiogram, pulse oximeter, glucose monitor, and the like. The data comprises data points indicative of additional health categories in which the user might be at risk. For example, these data points can indicate: obesity, diabetes, cancer, heart disease. These reports can be followed by employers, doctors, or other interested parties in making suggestions for activities to remediate or counteract these risks, including, for example, certain types of exercise or activities. Data input can come from sources in addition to the Patient Information Collection System 105 and the biometric data collection means.

For example, a patient is a 42-year-old obese truck driver and inputs responses into the Patient Information Collection System 105. The report is targeted in two simple ways: 1) based on the fact that the patient is a truck driver and a prevention strategy is identified to strengthen, stabilize and/or mobilize anatomic areas susceptible to injury in truck drivers; and 2) the patient is obese and a prevention strategy is identified including to movements and exercises for obese patients, e.g., recommendations for walking and similar tailored movement and activity. Accordingly, the report also includes recommended prevention strategies for walking type injuries.

In some examples, patient communication system 100 may match a user's (e.g., a customer's) common musculoskeletal condition or injury to a credible (e.g., evidence-based, clinical practice guideline-driven) treatment plan. Such matching may be based on user input via input device 110, second code segment 135, database 125, etc. Patient communications system 100 may implement client-driven clinical decision trees, health care provider interface options, and client self-care enhancement and self-responsibility facilitation strategies. In some examples, patient communications system 100 may thus offer a mechanism and structure to quickly and widely implement the recommendations provided within the AOPT/JOSPT clinical practice guidelines in a cost-effective manner.

Thus, the internationally recognized best care models for individuals with common musculoskeletal conditions may be delivered, without barriers, using a digital health platform implementing one or more aspects of the techniques described with reference to example patient communications system 100. The user's responses to questions or prompts of a clinical decision tree or clinical decision algorithm (e.g., which may be embedded in any digital interface, or may be performed manually using a paper survey for example), may be used to match the user's clinical presentation to the clinical guidelines-based recovery plan that is most effective for empowering the user to best care for, manage, and work toward alleviating annoying conditions or recent injuries. In some examples, this self-care may be supplemented by clinicians who are trained in the assessment and treatment of musculoskeletal conditions consistent with the clinical practice guidelines recommendations.

These strategies and processes may provide for a physical therapy implementation tool, which may available to clinicians who have access to the libraries or databases of digital guideline implementation strategies and processes described herein. In some cases, the content of this guideline implementation tool may not part of the curriculum of a physical therapy entry-level or continuing education seminar, unless student or clinician's training uses a digital platform, license, or some other access to such content. Thus, utilizing such a clinical practice guideline implementation tool, such as patient communications system 100, may be associated with access to a credible library or database 125 of healthcare information.

In accordance with some examples (e.g., based on the data the user inputs and the pattern the user's clinical profile matches), patient communication system 100 may assign an evidence-based proprietary recovery plan. In some cases, the exercise components of a plan may be built with specific strategies to provide the optimal therapeutic treatment dose to the user based upon the user's individual tissue tolerance and ability to respond to a health-enhancing physical load. In some cases, such self-adjusting exercise programs delivered by patient communications system 100 may continually adjust to the user's perceived exertion level, continually correcting the exercise level to be either at an easier or at a more difficult level based upon the user's feedback.

Additionally, all recovery plans may be coupled with tailored, health-literate education on what the user's condition or injury is. Recovery plans may include recommendations or strategies on how the user may get better (e.g., such as exercise information for the user based on user input). In some cases, health education components, like the exercise components, linked to each condition or injury may geared to implement the recommendations of the clinical practice guidelines where the typical focus is to facilitate a user's self-responsibility, confidence, and hope with managing their condition.

The outcomes of patient communication system 100 be used in several independent or combined ways. Many of these uses may be enhanced as the data can be stratified by the user demographic, specific condition, and outcome.

For example, as described herein, user input may further be leveraged for health maintenance, wellness, and injury prevention plans. These plans may use health education, ergonomic instruction and exercises to train users (e.g., clients) to reduce the areas susceptible to injuries related to specific work duties and recreational activities. Based on the work habits or most commonly associated movements and injuries associated with the job classification or recreational activity, patient communication system 100 (e.g., via database 125) may assign an evidence-based prevention plan. Additionally, the exercise component of determined prevention strategies may be stratified in such a manner that the end-user manages their own health by increasing or decreasing dosage of the treatment, through self-adjusting difficulty level, on their own accord.

In some cases, patient communication system 100 may tailor these plans specifically if patient communication system 100 has access to claims data that can show a pattern of common injury within a class or group (e.g., within a user demographic, within a workplace group, within an industry class, etc.). Additionally, all prevention plans may be coupled with job specific, health-literate education that may maintain health and prevent problems accordingly.

A database 125 may store data in a structured format. A database 125 may be structured as a single database 125, a distributed database 125, multiple distributed databases 125, or an emergency backup database 125. In some cases, a database 125 controller may manage data storage and processing in a database 125. In some cases, a user may interact with database 125 controller. In other cases, database 125 controller may operate automatically without user interaction.

In some cases, first output device 115, second output device 140, or both, may include or refer to a display. A display may comprise a conventional monitor, a monitor coupled with an integrated display, an integrated display (e.g., an LCD display), or other means for viewing associated data or processing information. Output devices other than the display can be used, such as printers, other computers or data storage devices, and computer networks. In some cases, first output device 115, second output device 140, or both, may include or refer to a speaker (e.g., for audible prompting of one or more user inputs).

In some cases, patient communication system 100 may include one or more processors (e.g., patient information collection system 105, database 125, patient clinical injury recovery system 130, and population targeting system 145 may each or together include or be coupled to one or more processors to implement one or more aspects of the techniques described herein). A processor may include an intelligent hardware device, (e.g., a general-purpose processing component, a digital signal processor (DSP), a central processing unit (CPU), a graphics processing unit (GPU), a microcontroller, an application specific integrated circuit (ASIC), a field programmable gate array (FPGA), a programmable logic device, a discrete gate or transistor logic component, a discrete hardware component, or any combination thereof).

In some cases, the processor may be configured to operate a memory array using a memory controller. In other cases, a memory controller may be integrated into the processor. The processor may be configured to execute computer-readable instructions stored in a memory to perform various functions. In some examples, a processor may include special purpose components for modem processing, baseband processing, digital signal processing, or transmission processing. In some examples, the processor may comprise a system-on-a-chip.

A user interface may enable a user to interact with a device. In some embodiments, the user interface may include an audio device, such as an external speaker system or microphone, an external display device such as a display screen, or an input device 110 (e.g., remote control device interfaced with the user interface directly or through an input/output (IO) controller module). In some cases, a user interface may be a graphical user interface (GUI).

An IO controller may manage input and output signals for a device. IO controller may also manage peripherals not integrated into a device. In some cases, an IO controller may represent a physical connection or port to an external peripheral. In some cases, an IO controller may utilize an operating system such as iOS®, ANDROID®, MS-DOS®, MS-WINDOWS®, OS/2®, UNIX®, LINUX®, or another known operating system. In other cases, an IO controller may represent or interact with a modem, a keyboard, a mouse, a touchscreen, or a similar device. In some cases, an IO controller may be implemented as part of a processor. In some cases, a user may interact with a device via IO controller or via hardware components controlled by an IO controller.

Figure 2:
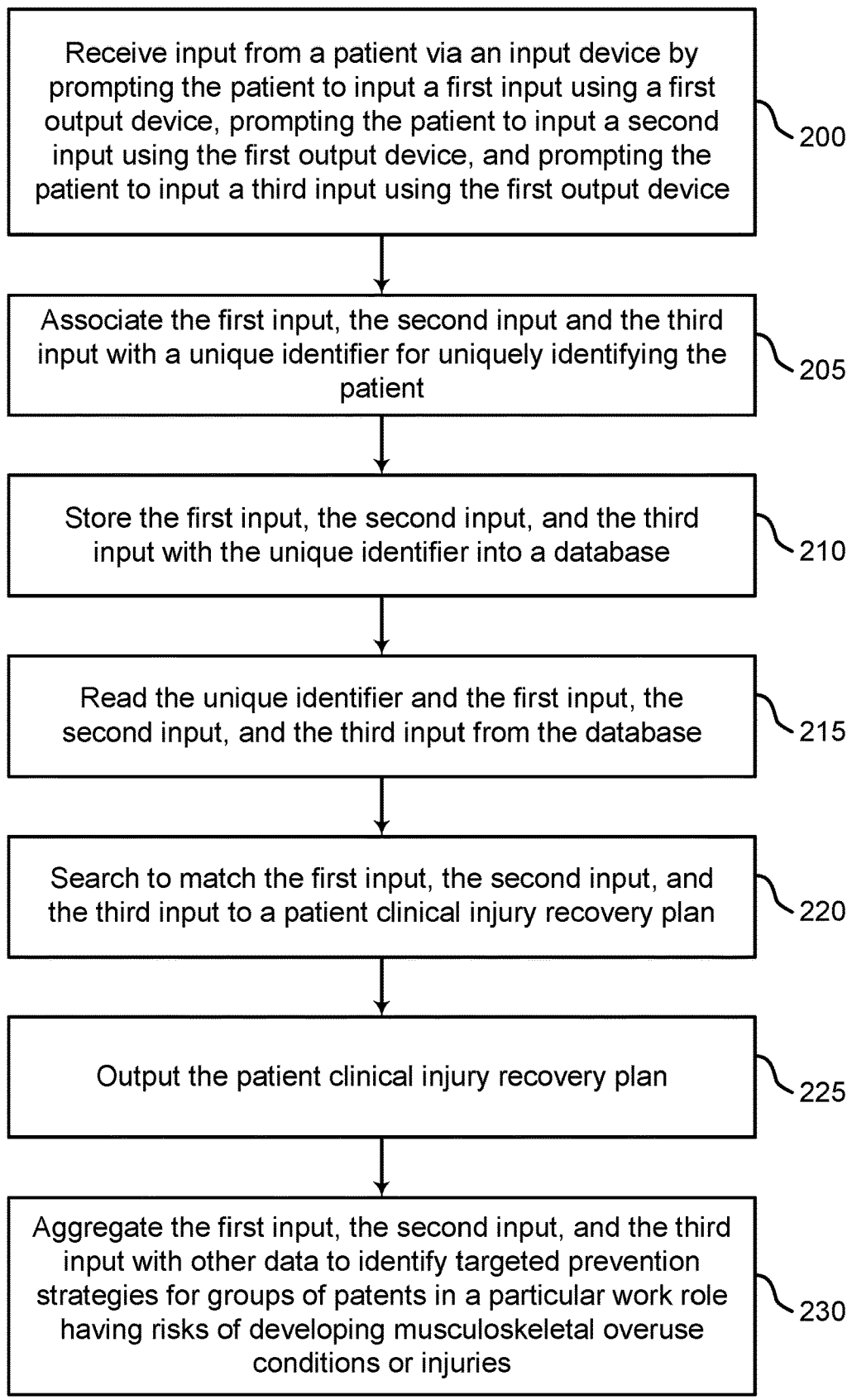
FIG. 2 shows an example of a process for patient communication according to aspects of the present disclosure.

FIG. 2 shows an example of a process for patient communication according to aspects of the present disclosure. In some examples, these operations may be performed by a system including a processor executing a set of codes to control functional elements of an apparatus. Additionally, or alternatively, the processes may be performed using special-purpose hardware. Generally, these operations may be performed according to the methods and processes described in accordance with aspects of the present disclosure. For example, the operations may be composed of various sub-steps, or may be performed in conjunction with other operations described herein.

At operation 200, the system receives input from a patient via an input device by prompting the patient to input a first input using a first output device, prompting the patient to input a second input using the first output device, and prompting the patient to input a third input using the first output device. In some cases, the operations of this step may refer to, or be performed by, a patient information collection system as described with reference to FIG. 1.

At operation 205, the system associates the first input, the second input and the third input with a unique identifier for uniquely identifying the patient. In some cases, the operations of this step may refer to, or be performed by, a patient clinical injury recovery plan generator as described with reference to FIG. 1.

At operation 210, the system stores the first input, the second input, and the third input with the unique identifier into a database. In some cases, the operations of this step may refer to, or be performed by, a database as described with reference to FIG. 1.

At operation 215, the system reads the unique identifier, the first input, the second input, and the third input from the database. In some cases, the operations of this step may refer to, or be performed by, a patient clinical injury recovery plan generator as described with reference to FIG. 1.

At operation 220, the system searches to match the first input, the second input, and the third input to a patient clinical injury recovery plan. In some cases, the operations of this step may refer to, or be performed by, a patient clinical injury recovery plan generator as described with reference to FIG. 1.

At operation 225, the system outputs the patient clinical injury recovery plan. In some cases, the operations of this step may refer to, or be performed by, a patient clinical injury recovery plan generator as described with reference to FIG. 1.

At operation 230, the system aggregates the first input, the second input, and the third input with other data to identify targeted prevention strategies for groups of patients in a particular work role having risks of developing musculoskeletal overuse conditions or injuries. In some cases, the operations of this step may refer to, or be performed by, a population targeting system as described with reference to FIG. 1.

FIG. 3 shows an example of a patient questions screen 305 according to aspects of the present disclosure. Screen display 300 may be an example of, or include aspects of, the corresponding element or elements described herein (e.g., with reference to FIGS. 1-7). Screen display 300 may include patient questions screen 305.

In some aspects, screen display 300 may correspond to first output device 115 and patient questions screen 305 may correspond to an example output of first output device 115. For instance, the screen display 300 may prompt a user to input one or more inputs (e.g., for processing by a patient communication system 100). The one or more user inputs may include answers to healthcare questions, selection of a body region, etc. In some cases, the healthcare questions may be based on a clinical decision tree managed by a database or library as described herein. In some cases, one or more aspects of the patient questions screen 305 may be managed or controlled by patient information collection system 105 (e.g., via first code segment 120).

Patient questions screen 305 may illustrate screen display 300 prompting of user input corresponding to user selection of a body part where a user is having problems. However, such is shown for illustrative purposes and one or more aspects of the described techniques may be modified by analogy, without departing from the scope of the present disclosure. For instance, screen display 300 may prompt a user to input text, audio, or other means of input, screen display 300 may prompt various other questions, etc., as described in more detail herein.

FIG. 4 shows an example of a patient clinical injury recovery plan 405 according to aspects of the present disclosure. Screen display 400 may be an example of, or include aspects of, the corresponding element or elements described herein (e.g., with reference to FIGS. 1-7). Screen display 400 may include recovery plan 405.

In some aspects, screen display 400 may correspond to second output device 140 and recovery plan 405 may correspond to an example output of second output device 140. For instance, the screen display 400 may display a recovery plan 405 determined based on one or more user inputs (e.g., based on answers to healthcare questions). In some cases, one or more aspects of the recovery plan 405 may be managed or controlled by patient clinical injury recovery system 130 (e.g., via second code segment 135). In some examples, screen display 400 may include a web browser. Recovery plan 405 may include relevant recovery plan information (e.g., exercises, videos, educational information, etc.) corresponding to a patient clinical injury.

Recovery plan 405 may illustrate screen display 400 providing a user with a shoulder instability recovery plan. However, such is shown for illustrative purposes and one or more aspects of the described techniques may be modified by analogy, without departing from the scope of the present disclosure. For instance, screen display 400 may provide other healthcare information, may be coupled with audio, etc., as described in more detail herein.

As an example, screen display 400 may provide various other recovery plans (e.g., based on user inputs). For instance, screen display may provide a neck stiffness plan. In such an example, health care information such as the following may be provided.

Neck Stiffness

From the information you provided, it sounds like you have a stiff, and maybe painful neck. Having a stiff neck can be bothersome and can limit your daily life. The condition can result from "sleeping wrong," from turning your head too quickly or awkwardly, or from the normal healing processes following an injury, such as a fall or a collision. Individuals often have pain primarily on one side of their neck and have a difficult time turning their head fully in one or more directions.

The joints and muscles in your neck work together to allow you to move freely. When a problem occurs in the joints in your upper back and neck, the muscles near the affected joints tend to tighten up to prevent you from moving your neck and further injuring yourself. This is helpful to promote healing for a couple of days; but afterward, those same muscles need to be trained to return to their normal ways of moving—without abnormal restrictions and pain. In the medical world, this stiffness between one vertebrae, or segment, of the spine and the adjacent segment is given the term "segmental mobility deficit."

What To Do!

A great way to deal with a stiff neck is to exercise, especially the stretching exercises that we provide for you. We suggest that you start with the Segmental SNAG that you perform sitting and the Diagonal and Side Neck Stretches that you perform while lying down—the Beginning Level exercises. With the Diagonal and Side Neck Stretches, a feeling of stretching or pulling while performing the exercises is fine, but you should not have intense pain during the stretching. Nor should you feel achy or stiff 20 minutes after you have finished your exercise routine. As shown in the videos, hold the stretches for about 30 seconds. After you feel comfortable with performing the stretching exercises while lying down, progress to performing the neck stretches in the sitting position—the Progressing Level exercises.

The shoulder instability recovery plan and neck stiffness plan described are done so for exemplary purposes. As discussed, various other healthcare information may be provided via screen display 400.

FIG. 5 shows an example of a clinician report 505 according to aspects of the present disclosure. Screen display 500 may be an example of, or include aspects of, the corresponding element or elements described herein (e.g., with reference to FIGS. 1-7). Screen display 500 may include clinician report 505.

In some aspects, screen display 500 may correspond to first output device 115 and clinician report 505 may correspond to an example output of first output device 115. In some examples, screen display 500 may correspond to second output device 140 and clinician report 505 may correspond to an example output of second output device 140. For instance, the screen display 500 may display a clinician report 505 to a user for input (e.g., via first code segment 120). In other examples, the screen display 500 may display a clinician report 505 to a clinician for review of a patient (e.g., via second code segment 135).

A clinician report 505 may be determined based on one or more user inputs (e.g., based on one or more user's answers to healthcare questions). In some examples, one or more aspects of the clinician report 505 may be managed or controlled by population targeting system 145 (e.g., via third code segment 150). In some examples, screen display 500 may include a web browser. Clinician report 505 may include relevant healthcare information. For instance, clinician report 505 may include patient input for a clinician review. In some cases, clinician report 505 may include preventative healthcare information (e.g., for clinicians, insurance groups, etc.) such as healthcare information corresponding to workplace groups, healthcare information corresponding to patient groups (e.g., certain patient demographics), etc.

Clinician report 505 may illustrate screen display 500 providing a clinician a report of a shoulder injury of a patient. However, such is shown for illustrative purposes and one or more aspects of the described techniques may be modified by analogy, without departing from the scope of the present disclosure. For instance, screen display 500 may provide various other clinician reports without departing from the scope of the present disclosure.

Figure 6:
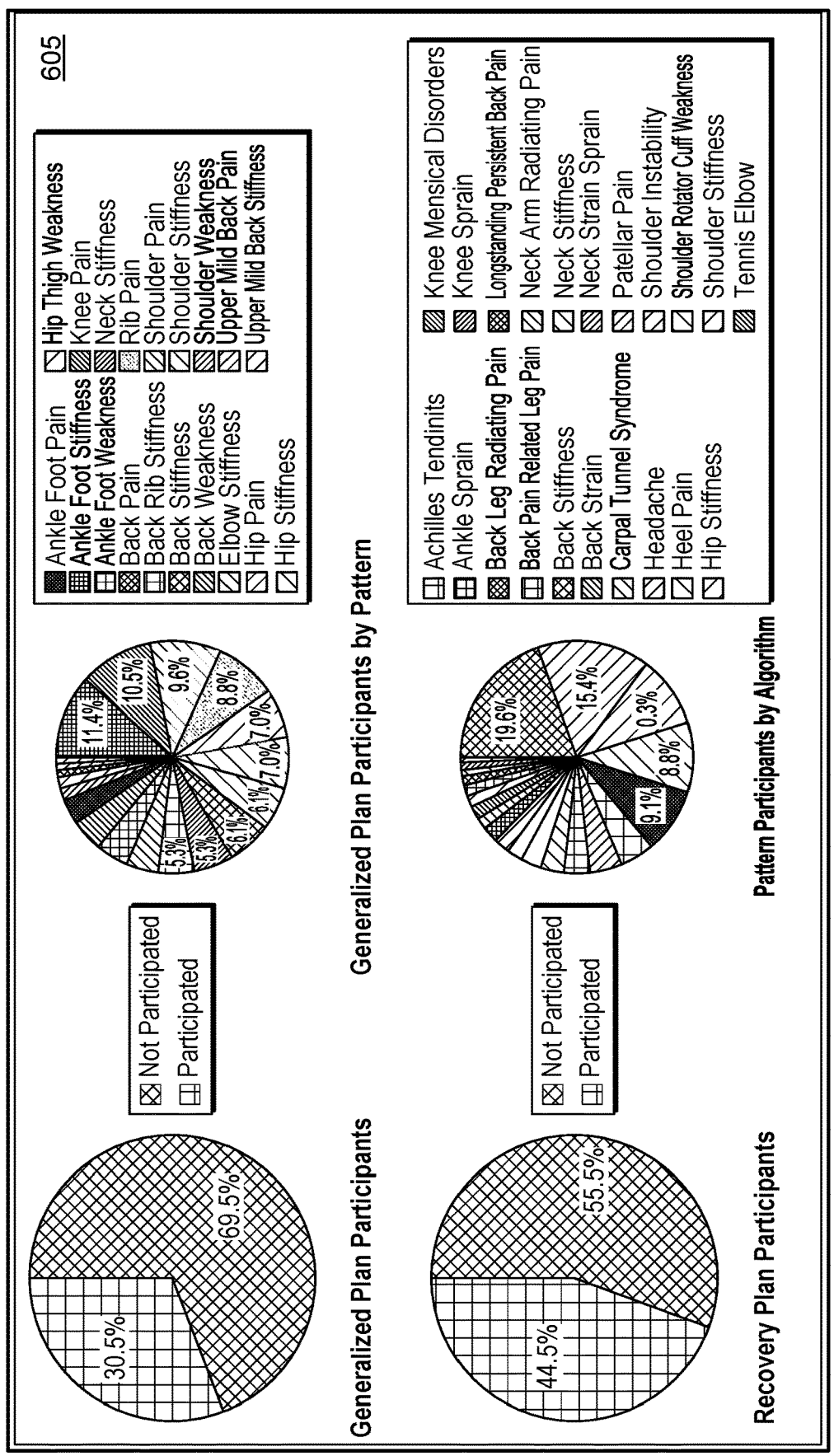
FIG. 6 shows an example of a population report according to aspects of the present disclosure.

FIG. 6 shows an example of a population report 605 according to aspects of the present disclosure. Screen display 600 may be an example of, or include aspects of, the corresponding element or elements described herein (e.g., with reference to FIGS. 1-7.) Screen display 600 may include population report 605.

In some examples, screen display 600 may correspond to second output device 140 and population report 605 may correspond to an example output of second output device 140. For instance, the screen display 600 may display a population report 605 to a clinician, insurance group, employer, etc. (e.g., via second code segment 135).

A population report 605 may be determined based on one or more user inputs (e.g., based on one or more user's answers to healthcare questions). In some examples, one or more aspects of the population report 605 may be managed or controlled by population targeting system 145 (e.g., via third code segment 150). In some examples, screen display 600 may include a web browser. Population report 605 may include relevant healthcare information. For instance, population report 605 may include preventative healthcare information (e.g., for clinicians, insurance groups, etc.). Population report 605 may include healthcare information corresponding to workplace groups, healthcare information corresponding to patient groups (e.g., certain patient demographics), etc.

Population report 605 may generally illustrate screen display 600 providing population-based, workplace-based, or other pattern-based healthcare information (e.g., which may be based on input from multiple users or multiple patients). However, such is shown for illustrative purposes and one or more aspects of the described techniques may be modified by analogy, without departing from the scope of the present disclosure. For instance, screen display 600 may provide various other population reports without departing from the scope of the present disclosure.

Figure 7:
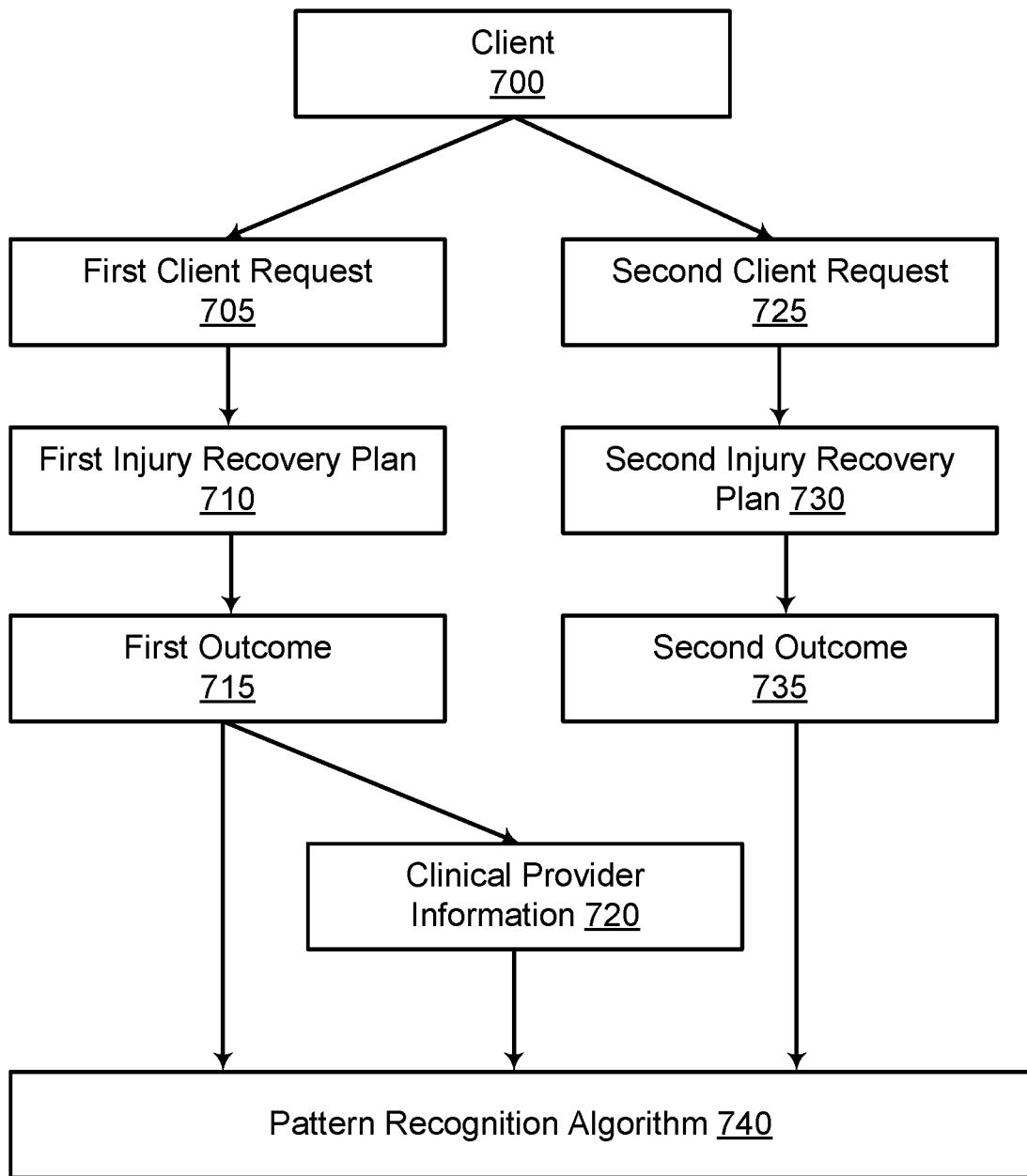
FIG. 7 shows an example of an injury recovery planning process according to aspects of the present disclosure.

FIG. 7 shows an example of an injury recovery planning process according to aspects of the present disclosure. The example shown includes client 700, first client request 705, first injury recovery plan 710, first outcome 715, clinical provider information 720, second client request 725, second injury recovery plan 730, second outcome 735, and pattern recognition algorithm 740.

The example injury recovery planning process of FIG. 7 may implement one or more aspects of an evidence-based, clinical practice guideline-driven, patient communication system (e.g., such as patient communication system 100) described herein. A client 700 may generally include a patient, a beneficiary, a consultant, an insurance company or insurance agent, or any user of the evidence-based, clinical practice guideline-driven, patient communication system.

The injury recovery planning process may provide for various healthcare applications. For instance, the injury recovery planning process may illustrate handling of example client requests including first client request 705 and second client request 725.

First client request 705 may include, for example, a request for assistance with musculoskeletal problems. In accordance with the techniques described herein, a first injury recovery plan 710 may be determined or derived based on the first client request. For example, based on first client request 705, the client 700 may be prompted (e.g., via an output device, such as via a display) to enter one or more inputs (e.g., answer one or more questions via an input device). Client-driven clinical decision trees, health care provider interface options, and client self-care enhancement and self-responsibility facilitation strategies may be implemented to provide a mechanism and structure for determination of first injury recovery plan 710.

In some examples, such techniques may be implemented to quickly and widely implement credible recommendations (e.g., a credible first injury recovery plan 710) in a cost-effective manner. A credible first injury recovery plan 710 may include healthcare recommendation plans provided within, or in accordance with, the AOPT/JOSPT clinical practice guidelines. For instance, as described herein, a database 125 may manage healthcare data collected from a large set of clients as well as data corresponding to AOPT/JOSPT guidelines. The database 125 may be leveraged by a patient communication system to determine first injury recovery plan 710 based on first client request 705, input from the client 700, etc., as described herein.

Accordingly, credible best care models for individuals with common musculoskeletal conditions may be delivered, without barriers, using a digital health platform implementing the described techniques. As used herein, "credible" healthcare may generally refer to evidence-based healthcare, clinical practice guideline-driven healthcare, internationally recognized best care models, healthcare in accordance with AOPT/JOSPT or other governing body guidelines, etc.

In some examples, inputs from a client 700 may include digitally entered responses to a clinical decision algorithm (e.g., which may be embedded in any digital interface), written or verbal responses input manually using a paper survey or questionnaire, etc. Inputs from a client 700 may be used to match the clinical presentation of the client 700 to the clinical guidelines-based recovery plan that is most effective for empowering the client 700 to best care for, manage, and work toward alleviating annoying conditions or recent injuries to the client 700. In some cases, this self-care may be supplemented by clinicians who are trained in the assessment and treatment of musculoskeletal conditions consistent with the clinical practice guidelines recommendations.

First outcome 715 may include or refer to various uses of the first injury recovery plan 710. For instance, as discussed, first outcome 715 may include client 700 usage of the first injury recovery plan 710 for self-care. Additionally, or alternatively, first outcome 715 may include usage of the first injury recovery plan 710 as a review tool, as a workforce targeted prevention tool, as a data collection tool, etc. That is, many uses of the first injury recovery plan 710 may be enhanced as the data (e.g., first client request 705, input from the client 700, etc.) may be stratified by the client demographic, specific condition and outcome.

In examples where the first outcome 715 includes usage of the first injury recovery plan 710 as a review utilization tool, the data collected about a clinical presentation of the client 700 may also be used as a utilization review tool to define needed approvals for visits within a payer group or insurance company.

In examples where the first outcome 715 includes usage of the first injury recovery plan 710 as a workforce targeted prevention tool, the data collected about a clinical presentation of the client 700 may be used by a company or employer to target prevention strategies for specific sub-groups of workers identified to be at risk for developing musculoskeletal overuse conditions or injuries.

In examples where the first outcome 715 includes usage of the first injury recovery plan 710 as a data collection tool, the data collected about a clinical presentation of the client 700 may be used to identify clients at risk for progressing toward disabling, chronic, and costly conditions. In some cases, the data collected about a clinical presentation of the client 700 may thus be used to identify clients that may would benefit from care pathways developed and implemented by payers and providers and clients to facilitate and support the client's movement toward health and optimal functioning.

Such patient management models may improve healthcare systems by providing for value-based care. For instance, the increased efficiency provided by the data collected and the immediate and progressive implementation options enabled by digital platforms implementing the described techniques may enable payers and practitioners to target their resources to the patient populations (e.g., client 700 populations) that may be most vulnerable (e.g., patients or clients 700 who may benefit from focused and effective health care).

In some examples, first injury recovery plan 710 may be utilized for clinical provider integration (e.g., as clinical provider information 720). The data collected about a clinical presentation of the client 700 (e.g., the clinical provider information 720) may be used, for example, by a clinician, brick and mortar establishment, telehealth provider, etc., to assist in evaluation of the client 700 to determine the client's optimal treatment strategies. As discussed herein, clinical provider information 720 may also be used in expediting intake and initial evaluations (e.g., by letting clinician know the likely injury before a consultation), used as a utilization tool for insurance groups (e.g., to help define pre-approved visit numbers and offer a significantly cheaper option for recovery), used as a tool to practices to take and manage contracts (e.g., contracts with strict visit limits, bundled payment, and capitations), used by offices and establishments to triage patients based on need or severity of injury, etc.

As discussed, the injury recovery planning process may provide for various healthcare applications and, in some aspects, may illustrate handling of example client requests including a second client request 725.

Second client request 725 may include, for example, a request for assistance with health maintenance, a request for assistance with injury prevention, etc. In accordance with the techniques described herein, a second injury recovery plan 730 may be determined or derived based on the second client request 725. For example, based on second client request 730, the client 700 may be prompted (e.g., via an output device, such as via a display) to enter one or more inputs (e.g., answer one or more questions via an input device). Client-driven clinical decision trees, health care provider interface options, and client self-care enhancement and self-responsibility facilitation strategies may be implemented to provide a mechanism and structure for determination of second injury recovery plan 730.

In some examples, such techniques may be implemented to quickly and widely implement credible recommendations (e.g., a credible second injury recovery plan 730) in a cost-effective manner. A credible second injury recovery plan 730 may include healthcare recommendation plans provided within, or in accordance with, the AOPT/JOSPT clinical practice guidelines. For instance, as described herein, a database 125 may manage healthcare data collected from a large set of clients as well as data corresponding to AOPT/JOSPT guidelines. The database 125 may be leveraged by a patient communication system to determine second injury recovery plan 730 based on second client request 725, input from the client 700, etc., as described herein.

In some examples, second injury recovery plan 730 may include health maintenance plans, wellness plans, injury prevention plans, etc. In some cases, second injury recovery plan 730 may include plans that use health education, ergonomic instruction, and exercises to train a client 700 to reduce the areas susceptible to injuries (e.g., which may be related to specific work duties and recreational activities). For instance, based on the work habits of most commonly associated movements and injuries associated with the job classification or recreational activity, the techniques described herein may be implemented to assign an evidence-based prevention plan. Additionally, an exercise component of the prevention strategies may be stratified in such a manner that the end-user (e.g., the client 700) manages their own health by increasing or decreasing dosage of the treatment, through self-adjusting difficulty level, on their own accord. Additionally, all prevention plans may be coupled with job specific, health-literate education to maintain health and prevent problems.

Second outcome 735 may include or refer to various uses of the second injury recovery plan 730. For instance, as discussed, second outcome 735 may include client 700 usage of the second injury recovery plan 730 for self-care. Additionally, or alternatively, second outcome 735 may include usage of the second injury recovery plan 730 as a review tool, as a workforce targeted prevention tool, as a data collection tool, etc. That is, many uses of the second injury recovery plan 730 may be enhanced as the data (e.g., second client request 725, input from the client 700, etc.) may be stratified by the client demographic, specific condition and outcome. For instance, first outcome 715, second outcome 735, or both, may include tailoring first injury recovery plan 710 and second injury recovery plan 730, respectively, if claims data is available that can indicate a pattern of common injury within a class or group.

Moreover, first outcome 715, second outcome 735, or both, may be associated with (or may be based on) a pattern recognition algorithm 740. Pattern recognition algorithm 740 (or pattern recognition techniques) may match a customer's common musculoskeletal condition or injury to the evidence-based, clinical practice guideline-driven best treatment plan. For instance, the clients' (e.g., the client 700's) responses to a clinical decision algorithm (e.g., which can be embedded in any digital interface) may be used to match the client's clinical presentation to the clinical guidelines-based recovery plan that is most effective for empowering the client to prevent, best care for, manage, and work toward alleviating annoying conditions or recent injuries. This self-care may, in some cases, be supplemented by clinicians or consultants who are trained in the assessment and treatment of musculoskeletal conditions consistent with the clinical practice guideline recommendations.

Figure 8:
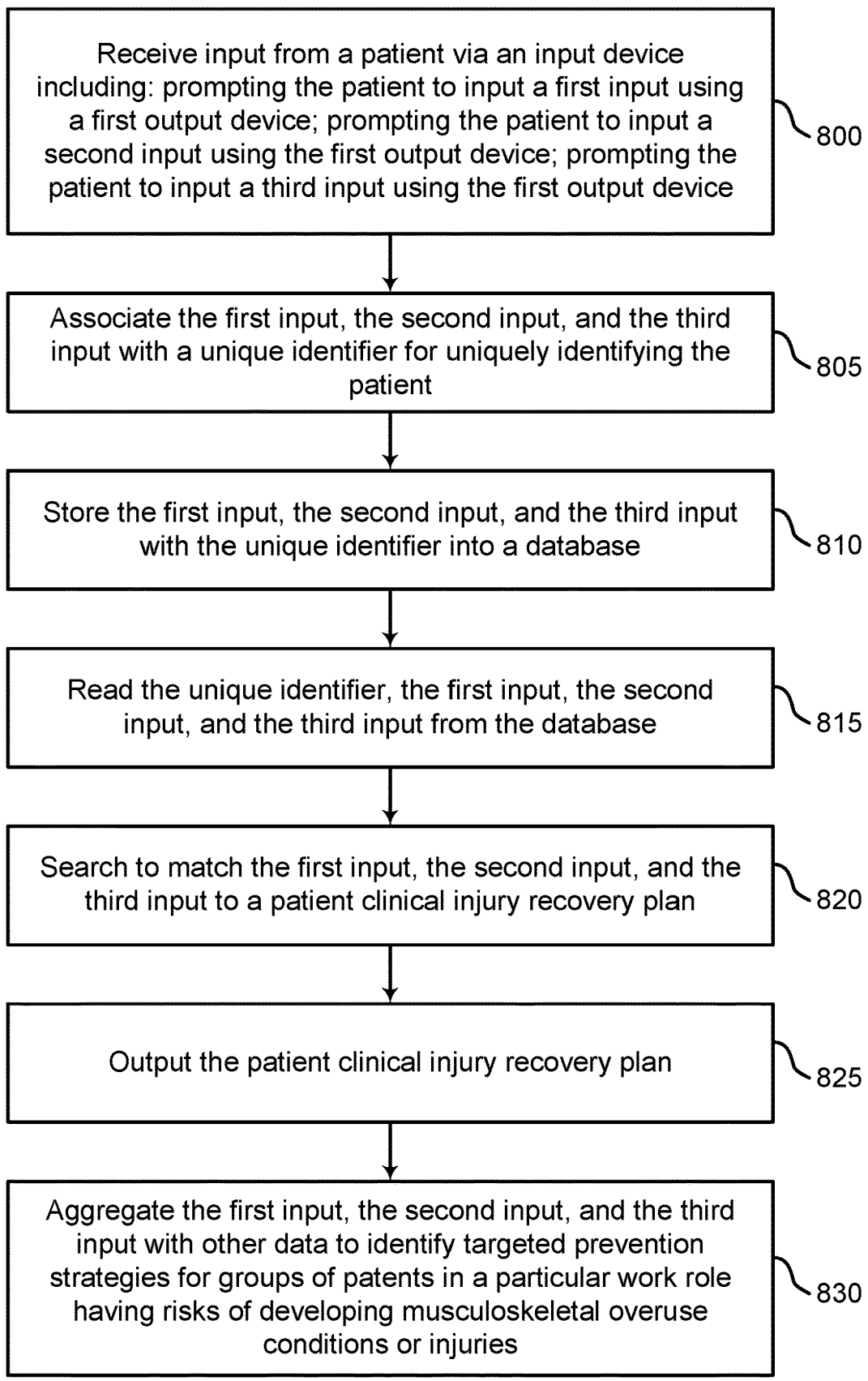
FIGS. 8 through 10 show examples of processes for evidence-based, clinical practice guideline-driven, patient communication according to aspects of the present disclosure.

FIG. 8 shows an example of a process for an evidence-based, clinical practice guideline-driven, patient communication according to aspects of the present disclosure. In some examples, these operations may be performed by a system including a processor executing a set of codes to control functional elements of an apparatus. Additionally, or alternatively, the processes may be performed using special-purpose hardware. Generally, these operations may be performed according to the methods and processes described in accordance with aspects of the present disclosure. For example, the operations may be composed of various sub-steps, or may be performed in conjunction with other operations described herein.

At operation 800, the system receives input from a patient via an input device including: prompting the patient to input a first input using a first output device; prompting the patient to input a second input using the first output device; prompting the patient to input a third input using the first output device. In some cases, the operations of this step may refer to, or be performed by, a patient information collection system as described with reference to FIG. 1.

At operation 805, the system associates the first input, the second input, and the third input with a unique identifier for uniquely identifying the patient. In some cases, the operations of this step may refer to, or be performed by, a patient information collection system as described with reference to FIG. 1.

At operation 810, the system stores the first input, the second input, and the third input with the unique identifier into a database. In some cases, the operations of this step may refer to, or be performed by, a database as described with reference to FIG. 1.

At operation 815, the system reads the unique identifier, the first input, the second input, and the third input from the database. In some cases, the operations of this step may refer to, or be performed by, a database as described with reference to FIG. 1.

At operation 820, the system searches to match the first input, the second input, and the third input to a patient clinical injury recovery plan. In some cases, the operations of this step may refer to, or be performed by, a database as described with reference to FIG. 1.

At operation 825, the system outputs the patient clinical injury recovery plan. In some cases, the operations of this step may refer to, or be performed by, a patient clinical injury recovery plan generator as described with reference to FIG. 1.

At operation 830, the system aggregates the first input, the second input, and the third input with other data to identify targeted prevention strategies for groups of patients in a particular work role having risks of developing musculoskeletal overuse conditions or injuries. In some cases, the operations of this step may refer to, or be performed by, a patient clinical injury recovery plan generator, a database, a population targeting system, or some combination thereof, as described with reference to FIG. 1.

Figure 9:
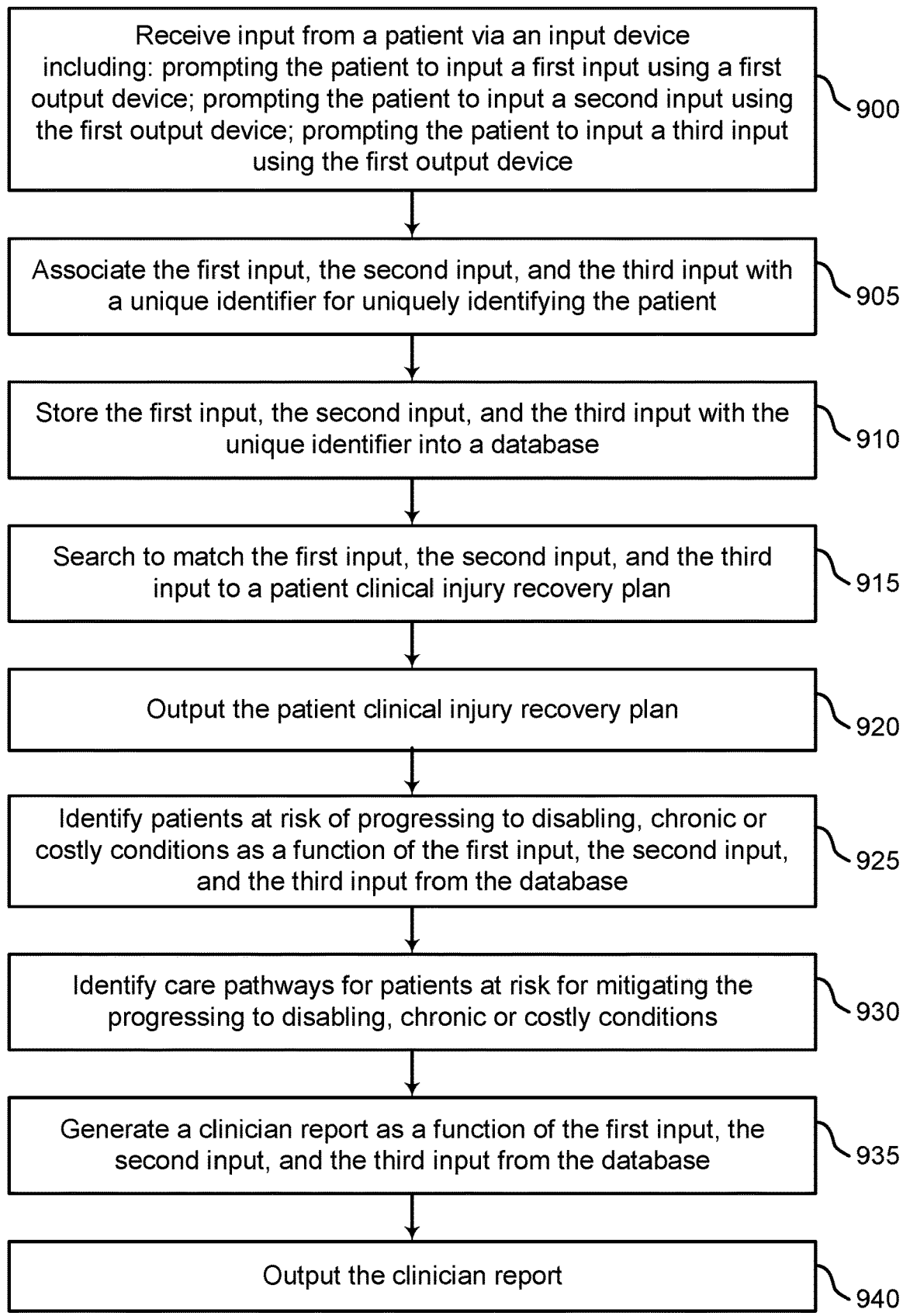

FIG. 9 shows an example of a process for an evidence-based, clinical practice guideline-driven, patient communication according to aspects of the present disclosure. In some examples, these operations may be performed by a system including a processor executing a set of codes to control functional elements of an apparatus. Additionally, or alternatively, the processes may be performed using special-purpose hardware. Generally, these operations may be performed according to the methods and processes described in accordance with aspects of the present disclosure. For example, the operations may be composed of various sub-steps, or may be performed in conjunction with other operations described herein.

At operation 900, the system receives input from a patient via an input device including: prompting the patient to input a first input using a first output device; prompting the patient to input a second input using the first output device; prompting the patient to input a third input using the first output device. In some cases, the operations of this step may refer to, or be performed by, a patient information collection system as described with reference to FIG. 1.

At operation 905, the system associates the first input, the second input, and the third input with a unique identifier for uniquely identifying the patient. In some cases, the operations of this step may refer to, or be performed by, a patient information collection system as described with reference to FIG. 1.

At operation 910, the system stores the first input, the second input, and the third input with the unique identifier into a database. In some cases, the operations of this step may refer to, or be performed by, a database as described with reference to FIG. 1.

At operation 915, the system searches to match the first input, the second input, and the third input to a patient clinical injury recovery plan. In some cases, the operations of this step may refer to, or be performed by, a database as described with reference to FIG. 1.

At operation 920, the system outputs the patient clinical injury recovery plan. In some cases, the operations of this step may refer to, or be performed by, a patient clinical injury recovery plan generator as described with reference to FIG. 1.

At operation 925, the system identifies patients at risk of progressing to disabling, chronic or costly conditions as a function of the first input, the second input, and the third input from the database. In some cases, the operations of this step may refer to, or be performed by, a database as described with reference to FIG. 1.

At operation 930, the system identifies care pathways for the patients at risk appropriate to mitigating the progressing to disabling, chronic or costly conditions. In some cases, the operations of this step may refer to, or be performed by, a patient clinical injury recovery plan generator, a database, a population targeting system, or some combination thereof, as described with reference to FIG. 1.

At operation 935, the system generates a clinician report as a function of the first input, the second input, and the third input from the database. In some cases, the operations of this step may refer to, or be performed by, a patient clinical injury recovery plan generator, a database, a population targeting system, or some combination thereof, as described with reference to FIG. 1.

At operation 940, the system outputs the clinician report. In some cases, the operations of this step may refer to, or be performed by, a patient clinical injury recovery plan generator, a database, a population targeting system, or some combination thereof, as described with reference to FIG. 1.

Figure 10:
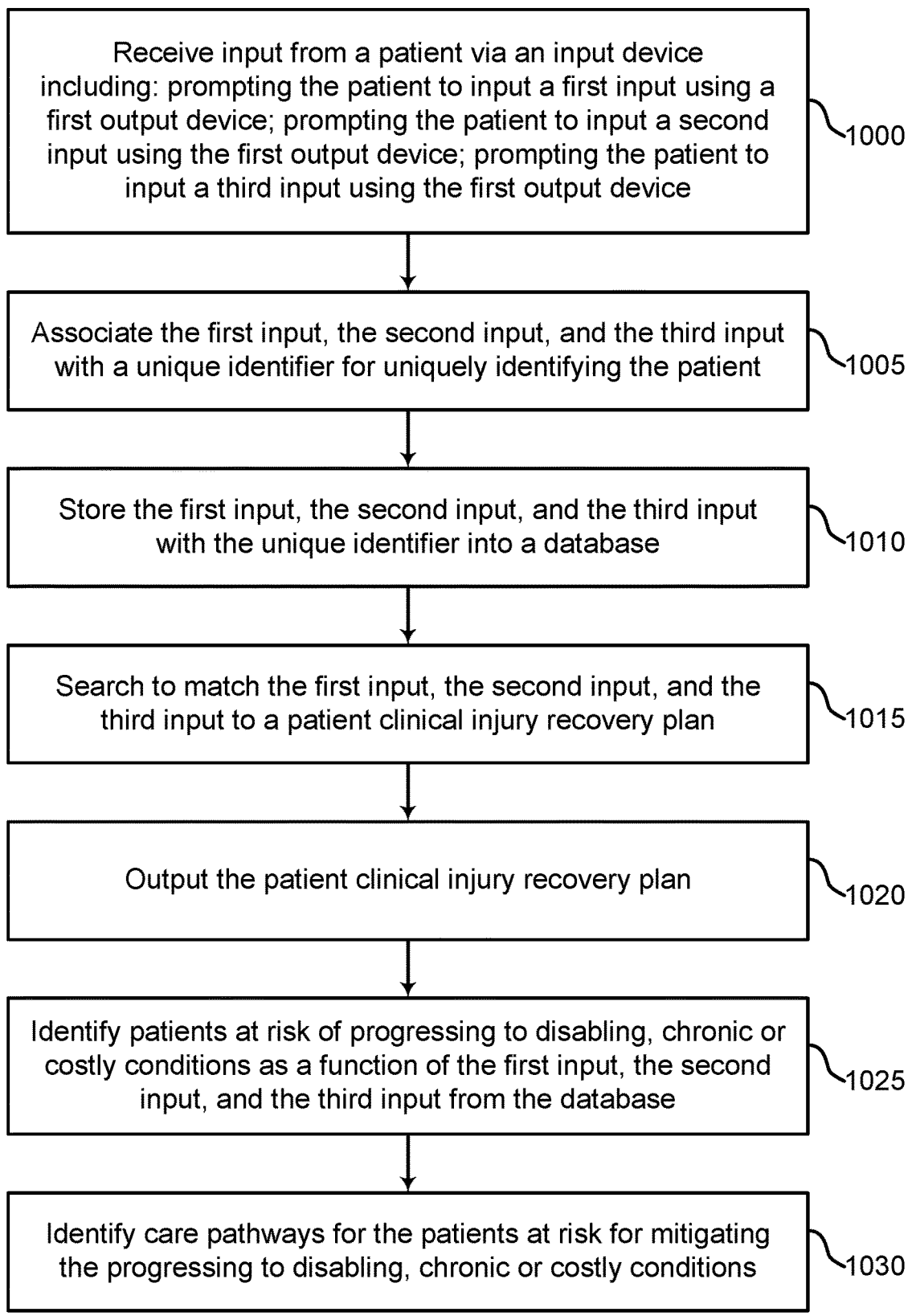

FIG. 10 shows an example of a process for an evidence-based, clinical practice guideline-driven, patient communication according to aspects of the present disclosure. In some examples, these operations may be performed by a system including a processor executing a set of codes to control functional elements of an apparatus. Additionally, or alternatively, the processes may be performed using special-purpose hardware. Generally, these operations may be performed according to the methods and processes described in accordance with aspects of the present disclosure. For example, the operations may be composed of various substeps, or may be performed in conjunction with other operations described herein.

At operation 1000, the system receives input from a patient via an input device including: prompting the patient to input a first input using a first output device; prompting the patient to input a second input using the first output device; prompting the patient to input a third input using the first output device. In some cases, the operations of this step may refer to, or be performed by, a patient information collection system as described with reference to FIG. 1.

At operation 1005, the system associates the first input, the second input, and the third input with a unique identifier for uniquely identifying the patient. In some cases, the operations of this step may refer to, or be performed by, a database as described with reference to FIG. 1.

At operation 1010, the system stores the first input, the second input, and the third input with the unique identifier into a database. In some cases, the operations of this step may refer to, or be performed by, a database as described with reference to FIG. 1.

At operation 1015, the system searches to match the first input, the second input, and the third input to a patient clinical injury recovery plan. In some cases, the operations of this step may refer to, or be performed by, a database as described with reference to FIG. 1.

At operation 1020, the system outputs the patient clinical injury recovery plan. In some cases, the operations of this step may refer to, or be performed by, a patient clinical injury recovery plan generator as described with reference to FIG. 1.

At operation 1025, the system identifies patients at risk of progressing to disabling, chronic or costly conditions as a function of the first input, the second input, and the third input from the database. In some cases, the operations of this step may refer to, or be performed by, a patient clinical injury recovery plan generator, a database, a population targeting system, or some combination thereof, as described with reference to FIG. 1.

At operation 1030, the system identifies care pathways for the patients at risk appropriate to mitigating the progressing to disabling, chronic or costly conditions. In some cases, the operations of this step may refer to, or be performed by, a patient clinical injury recovery plan generator, a database, a population targeting system, or some combination thereof, as described with reference to FIG. 1.

Accordingly, the present disclosure includes the following embodiments.

A system for an evidence-based, clinical practice guideline-driven, patient communication system is described. Embodiments of the system may provide for a patient information collection system including: an input device; a first output device; a first code segment, wherein the first code segment is coupled to the input device to receive input from a patient via the input device, and wherein the first code segment is coupled to the first output device, wherein the first code segment comprises a sequence of instructions, and wherein the sequence of instructions comprises: a first instruction to prompt the patient to input a first input using the first output device; a second instruction to prompt the patient to input a second input using the first output device; a third instruction to prompt the patient to input a third input using the first output device, a database coupled to the patient information collection system, wherein the first code segment associates the first input, the second input, and the third input with a unique identifier for uniquely identifying the patient, and stores the first input, the second input, and the third input with the unique identifier into the database, a patient clinical injury recovery plan generator coupled to the database, wherein the patient clinical injury recovery plan generator comprises: a second code segment, wherein the second code segment reads the unique identifier, the first input, the second input, and the third input from the database, and searches to match the first input, the second input, and the third input to a patient clinical injury recovery plan; and a second output device, wherein the second output device is configured to output the patient clinical injury recovery plan, and a population targeting system coupled to the database, wherein the population targeting system comprises: a third code segment, wherein the third code segment reads the unique identifier, the first input, the second input, and the third input from the database, reads other data from the database, and aggregates the first input, the second input, and the third input with the other data to identify targeted prevention strategies for groups of patients in a particular work role having risks of developing musculoskeletal overuse conditions or injuries.

In some examples, the patient clinical injury recovery plan generator is coupled to the database, wherein the patient clinical injury recovery plan generator comprises: the second code segment, wherein the second code segment reads the unique identifier, the first input, the second input, and the third input from the database, and searches to match the first input, the second input, and the third input to a patient clinical injury recovery plan, wherein, when the second code segment searches to match the first input, the second input, and the third input to a patient clinical injury recovery plan, no match to a patient clinical injury recovery plan is made and, in response to the no match to a clinical guidelines-based recovery plan being made, a clinician referral is generated.

In some examples, the patient clinical injury recovery plan generator is coupled to the database, wherein the patient clinical injury recovery plan generator comprises: the second output device, wherein the second output device is configured to output the patient clinical injury recovery plan, wherein the patient clinical injury recovery plan comprises at least one instructional video selected as a function of the first input, the second input, and the third input.

Some examples of the system described above may further include a payer approval system coupled to the database, wherein the payer approval system comprises: a fourth code segment, wherein the fourth code segment reads the unique identifier, the first input, the second input, and the third input from the database, and defines payer approvals needed for future patient visits to a healthcare provider in support of the patient clinical injury recovery plan.

Some examples of the system described above may further include a risk classifier system coupled to the database, wherein the risk classifier system comprises: a fourth code segment, wherein the fourth code segment reads the unique identifier, the first input, the second input, and the third input from the database, and identifies patients at risk of progressing to disabling, chronic or costly conditions and identifies care pathways appropriate to mitigating the progressing to disabling, chronic or costly conditions.

Some examples of the system described above may further include a clinician reporting system, wherein the clinician reporting system comprises; a fourth code segment, wherein the fourth code segment reads the unique identifier, the first input, the second input, and the third input from the database, and generates a clinician report; and a third output device, wherein the third output device is configured to output the clinician report.

A system for an evidence-based, clinical practice guideline-driven, patient communication system is described. Embodiments of the system may provide for a patient information collection system including: an input device; a first output device; a first code segment, wherein the first code segment is coupled to the input device to receive input from a patient via the input device, and wherein the first code segment is coupled to the first output device, wherein the first code segment comprises a sequence of instructions, and wherein the sequence of instructions comprises: a first instruction to prompt the patient to input a first input using the first output device; a second instruction to prompt the patient to input a second input using the first output device; a third instruction to prompt the patient to input a third input using the first output device, a database coupled to the patient information collection system, wherein the first code segment associates the first input, the second input, and the third input with a unique identifier for uniquely identifying the patient, and stores the first input, the second input, and the third input with the unique identifier into the database, a patient clinical injury recovery plan generator coupled to the database, wherein the patient clinical injury recovery plan generator comprises a second code segment, wherein the second code segment reads the unique identifier, the first input, the second input, and the third input from the database, and searches to match the first input, the second input, and the third input to a patient clinical injury recovery plan; and a second output device, wherein the second output device is configured to output the patient clinical injury recovery plan, a risk classifier system coupled to the database, wherein the risk classifier system comprises: a third code segment, wherein the third code segment reads the unique identifier, the first input, the second input, and the third input from the database, and identifies patients at risk of progressing to disabling, chronic or costly conditions and identifies care pathways appropriate to mitigating the progressing to disabling, chronic or costly conditions, and a clinician reporting system, wherein the clinician reporting system comprises: a fourth code segment, wherein the fourth code segment reads the unique identifier, the first input, the second input, and the third input from the database, and generates a clinician report; and a third output device, wherein the third output device is configured to output the clinician report.

In some examples, the patient clinical injury recovery plan generator is coupled to the database, wherein the patient clinical injury recovery plan generator comprises: the second code segment, wherein the second code segment reads the unique identifier, the first input, the second input, and the third input from the database, and searches to match the first input, the second input, and the third input to a patient clinical injury recovery plan, wherein, when the second code segment searches to match the first input, the second input, and the third input to a patient clinical injury recovery plan, no match to a patient clinical injury recovery plan is made and, in response to the no match to a clinical guidelines-based recovery plan being made, a clinician referral is generated.

In some examples, the patient clinical injury recovery plan generator is coupled to the database, wherein the patient clinical injury recovery plan generator comprises: the second output device, wherein the second output device is configured to output the patient clinical injury recovery plan, wherein the patient clinical injury recovery plan comprises at least one instructional video selected as a function of the first input, the second input, and the third input.

Some examples of the system described above may further include a payer approval system coupled to the database, wherein the payer approval system comprises: a fifth code segment, wherein the fifth code segment reads the unique identifier, the first input, the second input, and the third input from the database, and defines payer approvals needed for future patient visits to a healthcare provider in support of the patient clinical injury recovery plan.

Some examples of the system described above may further include a population targeting system coupled to the database, wherein the population targeting system comprises: a sixth code segment, wherein the sixth code segment reads the unique identifier, the first input, the second input, and the third input from the database, reads other data from the database, and aggregates the first input, the second input, and the third input with the other data to identify targeted prevention strategies for groups of patients in a particular work role having risks of developing musculoskeletal overuse conditions or injuries.

A system for an evidence-based, clinical practice guideline-driven, patient communication system is described. Embodiments of the system may provide for a patient information collection system including: an input device; a first output device; a first code segment, wherein the first code segment is coupled to the input device to receive input from a patient via the input device, and wherein the first code segment is coupled to the first output device, wherein the first code segment comprises a sequence of instructions, and wherein the sequence of instructions comprises: a first instruction to prompt the patient to input a first input using the first output device; a second instruction to prompt the patient to input a second input using the first output device; a third instruction to prompt the patient to input a third input using the first output device, a database coupled to the patient information collection system, wherein the first code segment associates the first input, the second input, and the third input with a unique identifier for uniquely identifying the patient, and stores the first input, the second input, and the third input with the unique identifier into the database, a patient clinical injury recovery plan generator coupled to the database, wherein the patient clinical injury recovery plan generator comprises: a second code segment, wherein the second code segment reads the unique identifier, the first input, the second input, and the third input from the database, and searches to match the first input, the second input, and the third input to a patient clinical injury recovery plan; and a second output device, wherein the second output device is configured to output the patient clinical injury recovery plan, a population targeting system coupled to the database, wherein the population targeting system comprises a third code segment, wherein the third code segment reads the unique identifier, and the first input, the second input and the third input from the database, reads other data from the database, and aggregates the first input, the second input, and the third input with the other data to identify targeted prevention strategies for groups of patients in a particular work role having risks of developing musculoskeletal overuse conditions or injuries, and a risk classifier system coupled to the database, wherein the risk classifier system comprises: a fourth code segment, wherein the fourth code segment reads the unique identifier, the first input, the second input, and the third input from the database, and identifies patients at risk of progressing to disabling, chronic or costly conditions and identifies care pathways appropriate to mitigating the progressing to disabling, chronic or costly conditions.

In some examples, the patient clinical injury recovery plan generator is coupled to the database, wherein the patient clinical injury recovery plan generator comprises: the second code segment, wherein the second code segment reads the unique identifier, the first input, the second input, and the third input from the database, and searches to match the first input, the second input, and the third input to a patient clinical injury recovery plan, wherein, when the second code segment searches to match the first input, the second input, and the third input to a patient clinical injury recovery plan, no match to a patient clinical injury recovery plan is made and, in response to the no match to a clinical guidelines-based recovery plan being made, a clinician referral is generated.

In some examples, the patient clinical injury recovery plan generator is coupled to the database, wherein the patient clinical injury recovery plan generator comprises: the second output device, wherein the second output device is configured to output the patient clinical injury recovery plan, wherein the patient clinical injury recovery plan comprises at least one instructional video selected as a function of the first input, the second input, and the third input.

Some examples of the system described above may further include a payer approval system coupled to the database, wherein the payer approval system comprises: a fifth code segment, wherein the fifth code segment reads the unique identifier, the first input, the second input, and the third input from the database, and defines payer approvals needed for future patient visits to a healthcare provider in support of the patient clinical injury recovery plan.

Some examples of the system described above may further include a clinician reporting system, wherein the clinician reporting system comprises: a sixth code segment, wherein the sixth code segment reads the unique identifier, the first input, the second input, and the third input from the database, and generates a clinician report; and a third output device, wherein the third output device is configured to output the clinician report.

Some examples of the method, apparatus, and non-transitory computer readable medium described above may further include generating a clinician referral when the searching to match the first input, the second input, and the third input to a patient clinical injury recovery plan, results in no match to a patient clinical injury recovery plan and, in response to the no match to a clinical guidelines-based recovery plan being made.

In some examples, the patient clinical injury recovery plan comprises at least one instructional video selected as a function of the first input, the second input, and the third input.

In some examples, the patient clinical injury recovery plan comprises at least one illustration selected as a function of the first input, the second input, and the third input.

In some examples, the patient clinical injury recovery plan comprises at least one audio file selected as a function of the first input, the second input, and the third input.

In some examples, the patient clinical injury recovery plan comprises at least one written instruction selected as a function of the first input, the second input, and the third input.

Some examples of the method, apparatus, and non-transitory computer readable medium described above may further include determining payer approval for future patient visits to a healthcare provider in support of the patient clinical injury recovery plan as a function of the first input, the second input, and the third input from the database.

Some examples of the method, apparatus, and non-transitory computer readable medium described above may further include identifying patients at risk of progressing to disabling, chronic or costly conditions as a function of the first input, the second input, and the third input from the database. Some examples may further include identifying care pathways for the patients at risk appropriate to mitigating the progressing to disabling, chronic or costly conditions.

Some examples of the method, apparatus, and non-transitory computer readable medium described above may further include generating a clinician report as a function of the first input, the second input, and the third input from the database. Some examples may further include outputting the clinician report.

Some examples of the method, apparatus, and non-transitory computer readable medium described above may further include generating a clinician referral when the searching to match the first input, the second input, and the third input to a patient clinical injury recovery plan, results in no match to a patient clinical injury recovery plan and, in response to the no match to a clinical guidelines-based recovery plan being made.

In some examples, the patient clinical injury recovery plan comprises at least one instructional video selected as a function of the first input, the second input, and the third input.

In some examples, the patient clinical injury recovery plan comprises at least one illustration selected as a function of the first input, the second input, and the third input.

In some examples, the patient clinical injury recovery plan comprises at least one audio file selected as a function of the first input, the second input, and the third input.

In some examples, the patient clinical injury recovery plan comprises at least one written instruction selected as a function of the first input, the second input, and the third input.

Some examples of the method, apparatus, and non-transitory computer readable medium described above may further include determining payer approval for future patient visits to a healthcare provider in support of the patient clinical injury recovery plan as a function of the first input, the second input, and the third input from the database.

Some examples of the method, apparatus, and non-transitory computer readable medium described above may further include identifying patients at risk of progressing to disabling, chronic or costly conditions as a function of the first input, the second input, and the third input from the database. Some examples may further include identifying care pathways for the patients at risk appropriate to mitigating the progressing to disabling, chronic or costly conditions.

Some examples of the method, apparatus, and non-transitory computer readable medium described above may further include generating a clinician referral when the searching to match the first input, the second input, and the third input to a patient clinical injury recovery plan, results in no match to a patient clinical injury recovery plan and, in response to the no match to a clinical guidelines-based recovery plan being made.

In some examples, the patient clinical injury recovery plan comprises at least one instructional video selected as a function of the first input, the second input, and the third input.

In some examples, the patient clinical injury recovery plan comprises at least one illustration selected as a function of the first input, the second input, and the third input.

In some examples, the patient clinical injury recovery plan comprises at least one audio file selected as a function of the first input, the second input, and the third input.

In some examples, the patient clinical injury recovery plan comprises at least one written instruction selected as a function of the first input, the second input, and the third input.

Some examples of the method, apparatus, and non-transitory computer readable medium described above may further include determining payer approval for future patient visits to a healthcare provider in support of the patient clinical injury recovery plan as a function of the first input, the second input, and the third input from the database.

Some examples of the method, apparatus, and non-transitory computer readable medium described above may further include generating a clinician report as a function of the first input, the second input, and the third input from the database. Some examples may further include outputting the clinician report.

While the invention herein disclosed has been described by means of specific embodiments, examples and applications thereof, numerous modifications and variations could be made thereto by those skilled in the art without departing from the scope of the invention set forth in the claims.

What is claimed is:

1. An evidence-based, clinical practice guideline-driven, patient communication system comprising:
   a patient information collection system including:
      an input device;
      a first output device;
      a first code segment, wherein the first code segment is coupled to the input device to receive input from a patient via the input device, and wherein the first code segment is coupled to the first output device, wherein the first code segment comprises a sequence of instructions, and wherein the sequence of instructions comprises:
         a first instruction, given via the first output device, to prompt the patient to input a first input
         a second instruction, given via the first output device, to prompt the patient to input a second input;
         a third instruction, given via the first output device, to prompt the patient to input a third input;
   a database coupled to the patient information collection system, wherein the first code segment associates the first input, the second input and the third input with a unique identifier for uniquely identifying the patient, and stores the first input, the second input, and the third input with the unique identifier into the database;
   a patient clinical injury recovery plan generator coupled to the database, wherein the patient clinical injury recovery plan generator comprises:
      a second code segment, wherein the second code segment includes a pattern recognition algorithm configured to read the unique identifier and the first input, the second input, and the third input from the database and determine whether the first input, the second input, and the third input matches to a patient clinical injury recovery plan and, upon the first input, the second input, and the third input matching to a patient clinical injury recovery plan, assigning the matched patient clinical injury recovery plan to the patient identifier; and
      a second output device, wherein the second output device is configured to output the patient clinical injury recovery plan in response to the second code segment matching the patient clinical injury recovery plan and output an indication that the patient should see a clinician or health care professional in response to second code segment determining that the first input, the second input, and the third input do not match to a patient clinical injury recovery plan;
   a population targeting system coupled to the database, wherein the population targeting system comprises:
      a third code segment, wherein the third code segment reads the unique identifier, and the first input, the second input and the third input from the database, reads other data from the database, and aggregates the first input, the second input, and the third input with the other data to identify targeted prevention strategies for groups of patients in a particular work role having risks of developing musculoskeletal overuse conditions or injuries.

2. The evidence-based, clinical practice guideline-driven, patient communication system of claim 1 further comprising:
said patient clinical injury recovery plan generator coupled to the database, wherein the patient clinical injury recovery plan generator comprises:
said second code segment, wherein said second code segment reads the unique identifier and the first input, the second input, and the third input from the database, and searches to match the first input, the second input, and the third input to a patient clinical injury recovery plan, wherein, when the second code segment searches to match the first input, the second input, and the third input to a patient clinical injury recovery plan, no match to a patient clinical injury recovery plan is made and, in response to the no match to a clinical guidelines-based recovery plan being made, a clinician referral is generated.

3. The evidence-based, clinical practice guideline-driven, patient communication system of claim 1 further comprising:
said patient clinical injury recovery plan generator coupled to the database, wherein the patient clinical injury recovery plan generator comprises:
said second output device, wherein the second output device is configured to output the patient clinical injury recovery plan, wherein said patient clinical injury recovery plan comprises at least one instructional video selected as a function of the first input, the second input, and the third input.

4. The evidence-based, clinical practice guideline-driven, patient communication system of claim 1 further comprising:
a payer approval system coupled to the database, wherein the payer approval system comprises:
a fourth code segment, wherein the fourth code segment reads the unique identifier, and the first input, the second input, and the third input from the database, and defines payer approvals needed for future patient visits to a healthcare provider in support of the patient clinical injury recovery plan.

5. The evidence-based, clinical practice guideline-driven, patient communication system of claim 1 further comprising:
a risk classifier system coupled to the database, wherein the risk classifier system comprises:
a fourth code segment, wherein the fourth code segment reads the unique identifier, and the first input, the second input, and the third input from the database, and identifies patients at risk of progressing to disabling, chronic or costly conditions and identifies care pathways appropriate to mitigating the progressing to disabling, chronic or costly conditions.

6. The evidence-based, clinical practice guideline-driven, patient communication system of claim 1 further comprising:
a clinician reporting system, wherein the clinician reporting system comprising;
a fourth code segment, wherein the fourth code segment reads the unique identifier, and the first input, the second input and the third input from the database, and generates a clinician report; and
a third output device, wherein the third output device is configured to output the clinician report.

7. The evidence-based, clinical practice guideline-driven, patient communication system of claim 1, wherein the first code segment further comprises a clinical decision algorithm configured to determine the second instruction and third instruction using at least the first input as input to the clinical decision algorithm.

8. An evidence-based, clinical practice guideline-driven, patient communication method comprising:
receiving input from a patient via an input device comprising:
prompting the patient, via a first output device, to input a first input;
prompting the patient, via a first output device, to input a second input;
prompting the patient, via a first output device, to input a third input;
associating, by a first code segment, the first input, the second input and the third input with a unique identifier for uniquely identifying the patient;
storing, by the first code segment, the first input, the second input, and the third input with the unique identifier into a database;
reading, by a second code segment including a pattern recognition algorithm, the unique identifier and the first input, the second input, and the third input from the database;
determining, by the second code segment, whether the first input, the second input, and the third input matches to a patient clinical injury recovery plan;
upon determining that a patient clinical recovery plan matches the inputs, assigning, by the second code segment, the matched patient clinical injury recovery plan to the patient identifier;
outputting, by a second output device, the patient clinical injury recovery plan in response to the second code segment matching the patient clinical injury recovery plan and output an indication that the patient should see a clinician or health care professional in response to second code segment determining that the first input, the second input, and the third input do not match to a patient clinical injury recovery plan; and
aggregating, by a third code segment, the first input, the second input, and the third input with other data to identify targeted prevention strategies for groups of patents in a particular work role having risks of developing musculoskeletal overuse conditions or injuries.

9. The evidence-based, clinical practice guideline-driven, patient communication method of claim 8 further comprising:
said searching to match the first input, the second input, and the third input to a patient clinical injury recovery plan, wherein, when the searching to match the first input, the second input, and the third input to a patient clinical injury recovery plan, results in no match to a patient clinical injury recovery plan and, in response to the no match to a clinical guidelines-based recovery plan being made, generating a clinician referral.

10. The evidence-based, clinical practice guideline-driven, patient communication method of claim 8 further comprising:
said outputting the patient clinical injury recovery plan, wherein said patient clinical injury recovery plan comprises at least one instructional video selected as a function of the first input, the second input, and the third input.

11. The evidence-based, clinical practice guideline-driven, patient communication method of claim 8 further comprising:
said outputting the patient clinical injury recovery plan, wherein said patient clinical injury recovery plan comprises at least one illustration selected as a function of the first input, the second input, and the third input.

12. The evidence-based, clinical practice guideline-driven, patient communication method of claim 8 further comprising:
said outputting the patient clinical injury recovery plan, wherein said patient clinical injury recovery plan comprises at least one audio file selected as a function of the first input, the second input, and the third input.

13. The evidence-based, clinical practice guideline-driven, patient communication method of claim 8 further comprising:
said outputting the patient clinical injury recovery plan, wherein said patient clinical injury recovery plan comprises at least one written instruction selected as a function of the first input, the second input, and the third input.

14. The evidence-based, clinical practice guideline-driven, patient communication method of claim 8 further comprising:
determining, by a payer approval system coupled to the database, wherein the payer approval system comprises a fourth code segment, payer approval for future patient visits to a healthcare provider in support of the patient clinical injury recovery plan as a function of the first input, the second input, and the third input from the database.

15. The evidence-based, clinical practice guideline-driven, patient communication method of claim 8 further comprising:
identifying, by a risk classifier system coupled to the database, wherein the risk classifier system comprises a fourth code segment, patients at risk of progressing to disabling, chronic or costly conditions as a function of the first input, the second input, and the third input from the database; and
identifying care pathways for the patients at risk appropriate to mitigating the progressing to disabling, chronic or costly conditions.

16. The evidence-based, clinical practice guideline-driven, patient communication method of claim 8 further comprising:
generating, by a clinician reporting system, wherein the clinician reporting system comprises a fourth code segment, a clinician report as function of the first input, the second input, and the third input from the database; and
outputting the clinician report.

\* \* \* \* \*